(12) United States Patent
Volovitz et al.

(10) Patent No.: US 8,741,315 B2
(45) Date of Patent: Jun. 3, 2014

(54) METHODS OF TREATING TUMORS IN IMMUNE-PRIVILEGED SITES

(75) Inventors: Ilan Volovitz, Tel-Aviv (IL); Lea Eisenbach, Rehovot (IL); Irun R. Cohen, Rehovot (IL); Zvi Ram, Ramat-Gan (IL); Shimon Slavin, Tel-Aviv (IL)

(73) Assignees: Yeda Research and Development Co. Ltd., Rehovot (IL); The Medical Research, Infrastructure and Health Services Fund of the Tel Aviv Medical Center, Tel-Aviv (IL)

( * ) Notice: Subject to any disclaimer, the term of this patent is extended or adjusted under 35 U.S.C. 154(b) by 776 days.

(21) Appl. No.: 12/677,543

(22) PCT Filed: Sep. 11, 2008

(86) PCT No.: PCT/IL2008/001215
§ 371 (c)(1),
(2), (4) Date: Mar. 11, 2010

(87) PCT Pub. No.: WO2009/034574
PCT Pub. Date: Mar. 19, 2009

(65) Prior Publication Data
US 2010/0189750 A1 Jul. 29, 2010

Related U.S. Application Data

(60) Provisional application No. 60/960,041, filed on Sep. 12, 2007.

(51) Int. Cl.
*A61K 39/00* (2006.01)
*A61K 35/30* (2006.01)

(52) U.S. Cl.
USPC ........................................ 424/277.1; 424/573

(58) Field of Classification Search
None
See application file for complete search history.

(56) References Cited

U.S. PATENT DOCUMENTS

| | | | |
|---|---|---|---|
| 6,207,147 B1 | 3/2001 | Hiscodt et al. | |
| 2001/0038841 A1* | 11/2001 | Hiserodt et al. | 424/130.1 |
| 2005/0063995 A1 | 3/2005 | Spaner et al. | |
| 2005/0196340 A1* | 9/2005 | Holash et al. | 424/1.69 |
| 2005/0239897 A1* | 10/2005 | Pittenger et al. | 514/569 |

FOREIGN PATENT DOCUMENTS

| | | |
|---|---|---|
| CN | 1355709 | 6/2002 |
| CN | 1774255 | 5/2006 |
| EP | 1159967 | 12/2001 |
| WO | WO9302556 | * 2/1993 |
| WO | WO 03/072032 | 9/2003 |
| WO | WO 2007/085648 | 8/2007 |

OTHER PUBLICATIONS

The abstract of Naujocks (International Journal of Oncology, 1995, vol. 6, No. 4, pp. 759-765).*
Farr-Jones et al (Journal of Neuro-Oncology, 1999, vol. 43, pp. 1-10).*
Naujocks et al (International Journal of Oncology, 1995, vol. 6, pp. 759-765).*
Chen et al "Living T9 Glioma Cells Expressing Membrane Macrophage Colony-Stimulating Factor Produce Immediate Tumor Destruction by Polymorphonuclear Leukocytes and Macrophages Via A 'Paraptosis'—Induced Pathway That Promotes Systemic Immunity Against Intracranial T9 Gliomas", Retrieved From the Internet at Weizmann Institute of Science, Blood, 100: 1373-1380, 2002.
Holladay et al. "Autologous Tumor Cell Vaccination Combined With Adoptive Cellular Immunotherapy in Patients With Grade III/IV Astrocytoma", Journal of Neuro-Oncology, 27(2): 179-189, Feb. 1996. p. 181-182, Sections: 'Tumor Processing', 'Tumor Vaccine Preparation and Immunization'.
Hoover et al. "Delayed Cutaneous Hypersensitivity to Autologous Tumor Cells in Colorectal Cancer Patients Immunized With an Autologous Tumor Cell: Bacillus Calmette-Guérin Vaccine", Cancer Research, 44: 1671-1676, Apr. 1984. p. 1671, Right Col., § 3.
Kalman et al "Immunopathogenic Mechanisms in Experimental Allergic Enceohalomyelitis",Current Opinion in Neurology and Neurosurgery, 6(2): 182-188, Apr. 1993. Abstract.
Sampson et al. "Subcutaneous Vaccination With Irradiated, Cytokine-Producing Tumor Cells Stimulates CD8+ Cell-Mediated Immunity Against Tumors Located in the 'Immunologically Privileged' Central Nervous System", Proc. Natl. Acad. Sci. USA, 93: 10399-10404, Sep. 1996.
Supplementary European Search Report and the European Search Opinion Dated Feb. 8, 2012 From the European Patent Office Re. Application No. 08789875.5.
Bullard et al. "A Preliminary Study Utilizing Viable HLA Mismatched Cultured Glioma Cells as Adjuvant Therapy for Patients With Malignant Gliomas", British Journal of Cancer, XP009155752, 51(2): 283-289, Jan. 1, 1985. p. 284, col. 1, Para 2-3.
Wikstrand et al. "Immunobiologic aspects of the Brain and Human Gliomas. A Review", American Journal of Pathology, XP055017443, 98(2): 517-568, Jan. 1, 1980. Table 3, p. 547, Para 3—p.551, Para 1.
Wood et al. "A Pilot Study of Autologous Cancer Cell Vaccination and Cellular Immunotherapy Using Anti-CD3 Stimulated Lymphocytes in Patients With Recurrent Grade III/IV Astrocytoma", Journal of Neuro-Oncology, XP055017445, 48(2): 113-120, Jun. 1, 2000. p. 114, col. 2, Para 2-3.

(Continued)

*Primary Examiner* — Karen Canella

(57) ABSTRACT

A method of treating cancer in an immune-privileged site of a subject in need thereof is provided. The method comprises systemically administering to an area outside the immune-privileged site of the subject, a therapeutically effective amount of naive, viable cells of a tumor of the subject, the tumor being in the immune-privileged site so as to generate an immune response in the subject, thereby treating the cancer in the immune-privileged site of the subject.

15 Claims, 21 Drawing Sheets
(11 of 21 Drawing Sheet(s) Filed in Color)

(56) References Cited

OTHER PUBLICATIONS

International Search Report Dated Jan. 27, 2009 From the International Searching Authority Re.: Application No. PCT/IL08/01215.
Written Opinion Dated Jan. 27, 2009 From the International Searching Authority Re.: Application No. PCT/IL08/01215.
Chen et al "Living T9 Glioma Cells Expressing Membrane Macrophage Colony-Stimulating Factor Produce Immediate Tumor Destruction by Polymorphonuclear Leukocytes and Macrophages via A "paraptosis"—Induced Pathway That Promotes Systemic Immunity Against Intracran ial T9 Gliomas", www.bloodjournal.org at Weizmann Instirute of Science, Sep. 11, 2008; Blood 100:1373-1380, 2002.
Eggers et al. "In Vivo Immunization Against Autologous Glioblastoma-Associated Antigens", Cancer Immunology Immunotherapy, 19: 43-45, 1985. p. 43, Right col., § 2-3.
Frost et al. "Tumor Immunoprophylaxis in Mice Using Glutaraldehyde-Treated Syngeneic Tumor Cells", Cancer Research, 35: 2646-2650, Oct. 1975. p. 2647, Right col., § 1.
Graf et al; "Contrasting Effects of Interleukin-2 Secretion by Rat Glioma Cells Contingent Upon Anatomical Location: Accelerated Tumorigenesis in the Central Nervous System and Complete Rejection in the Periphery", Journal of NeuroImmunology 140:49-60, 2003.
Kalman et al "Immunopathogenic Mechanisms in Experimental Allergic Enceohalomyelitis",Curr Opin Neurol Neurosurg, 6(2):182-8, Apr. 1993—National Institute for Neurology and Psychiatry, Budapaest, Hungary, (abstract only).
Mitchell "Relapse in the Central Nervous System in Melanoma Patients Sucessfully Treated With Biomodulators", Journal of Clinical Oncology, 7(11):1701-1709, Nov. 1989.
Peng et al. "Helper-Independent, L-Selection low CD8+ T Cells With Broad Anti-Tumor Efficacy Are Naturally Sensitized During Tumor Progression", The Joural of Immunology, 165:5738-5749, 2000.
Sampson "Meeting Report. The Preuss Foundation Seminar on Vaccine Therapy for Malignant Primary Brain Tumors", Neuro-Oncology, p. 33-42, Jan. 1999. Left col., § 1, p. 38, Right col., § 3.
Sampson et al. "Subcutaneous Vaccination With Irradiated, Cytokine-Producing Tumor Cells Stimulates CD8+ Cell-Mediated Immunity Against Tumors Located in the "Immunologically Privileged" Central Nervous System", Proc.Natl. Acad. Sci. 93:10399-10404, Sep. 1996.
Communication Pursuant to Article 94(3) EPC Dated Sep. 18, 2012 From the European Patent Office Re. Application No. 08789875.5.
Translation of Office Action Dated Aug. 27, 2012 From the State Intellectual Property Office of the People's Republic of China Re. Application No. 200880116440.6.
Translation of Search Report Dated Aug. 27, 2012 From the State Intellectual Property Office of the People's Republic of China Re. Application No. 200880116440.6.
Office Action Dated From Sep. 3, 2012 the Israel Patent Office Re. Application No. 204454 and Its Translation Into English.
Office Action Dated May 26, 2013 From the Israel Patent Office Re. Application No. 204454 and Its Translation Into English.
Translation of Office Action Dated Apr. 28, 2013 From the State Intellectual Property Office of the People's Republic of China Re. Application No. 200880116440.6.
Translation of Search Report Dated Apr. 28, 2013 From the State Intellectual Property Office of the People's Republic of China Re. Application No. 200880116440.6.
Examination Report Dated Jan. 24, 2013 From the Australian Government, IP Australia Re. Application No. 2008299318.
Decision on Rejection Dated Nov. 21, 2013 From the State Intellectual Property Office of the People's Republic of China Re. Application No. 200880116440.6 and Its Translation Into English.

* cited by examiner

FIGs. 2A-C

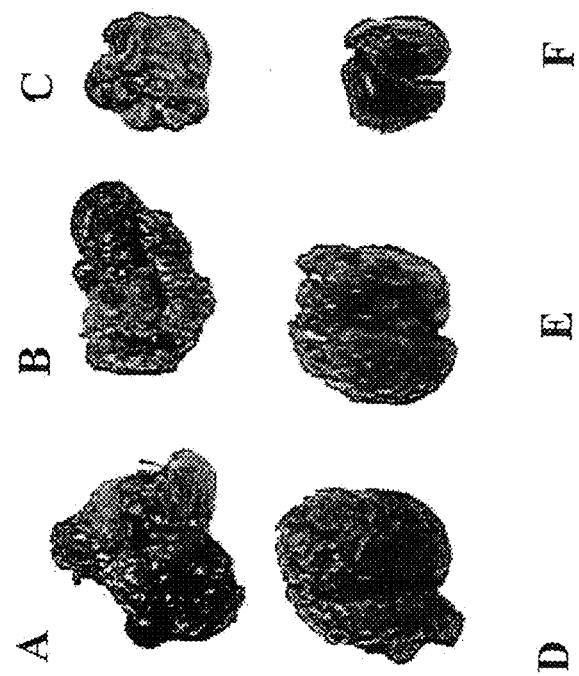
FIGs. 4A-F

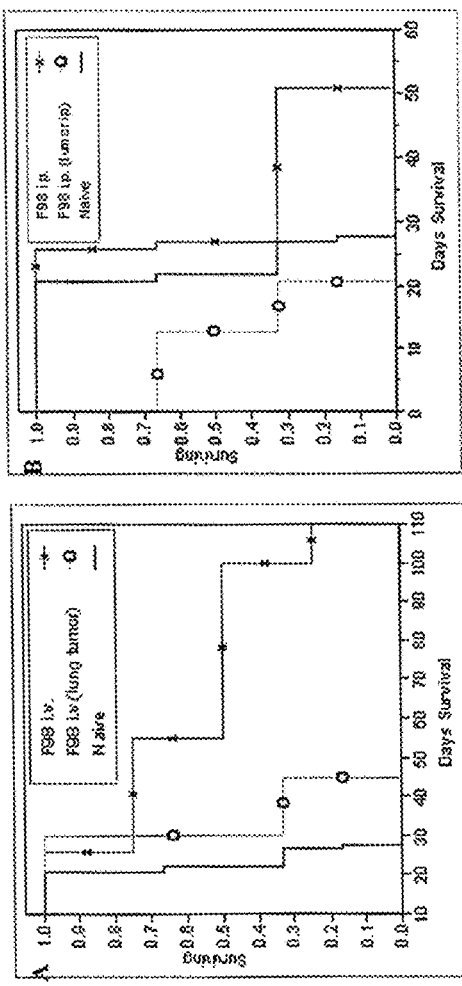
FIGs. 5A-B

FIGs. 6A-B
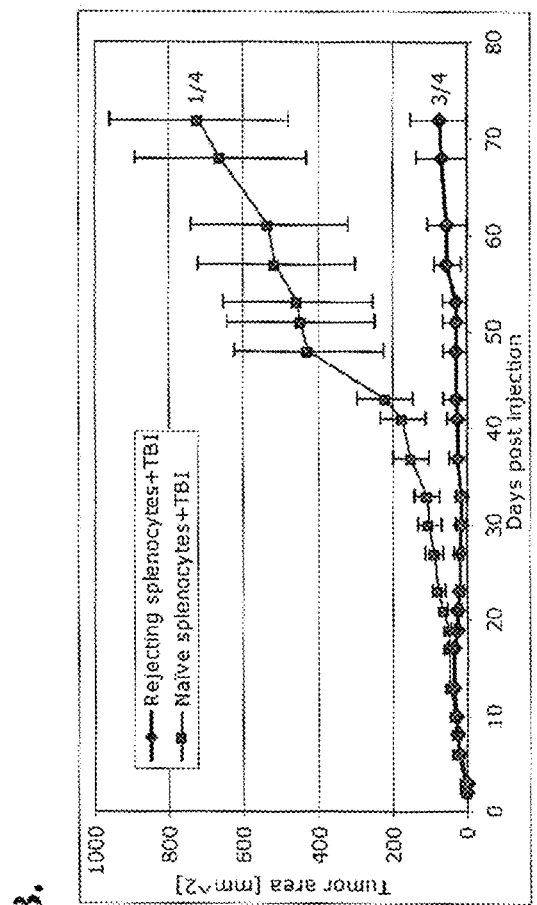
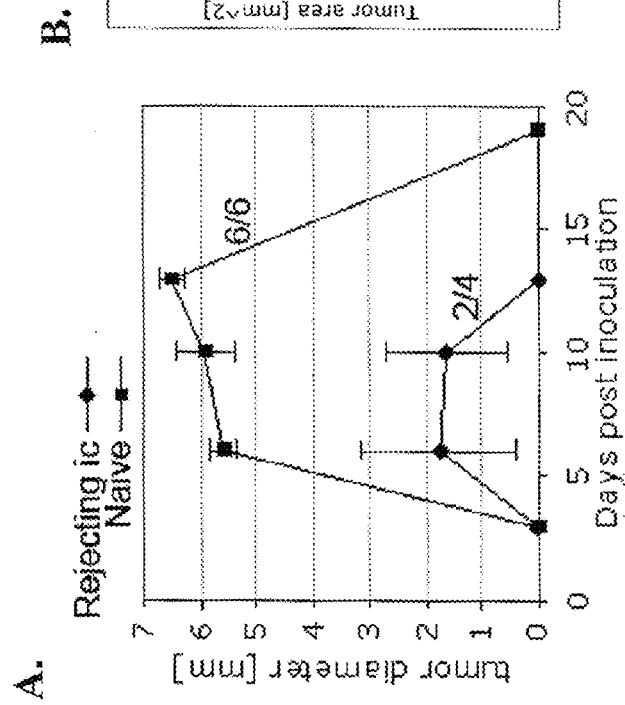

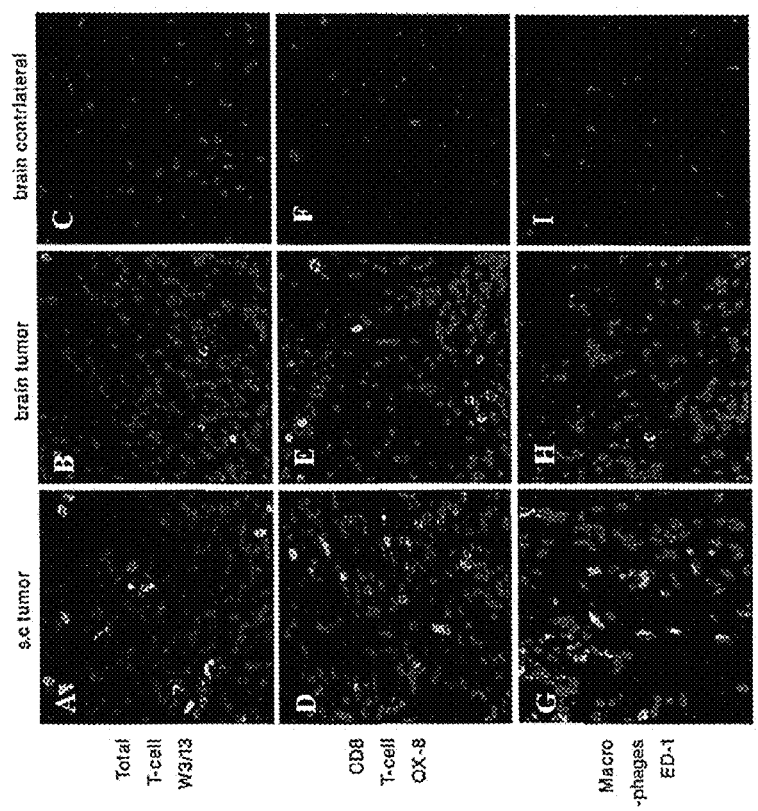
FIGs. 12A-I

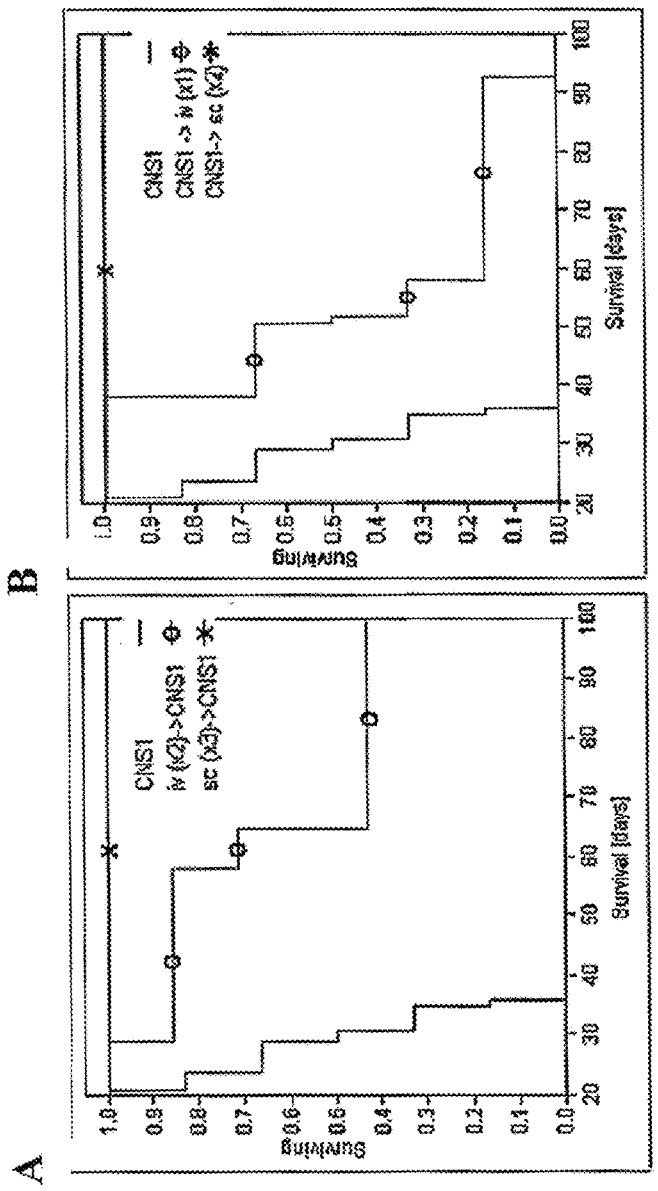
FIGs. 13A-B

FIGS. 14A-B
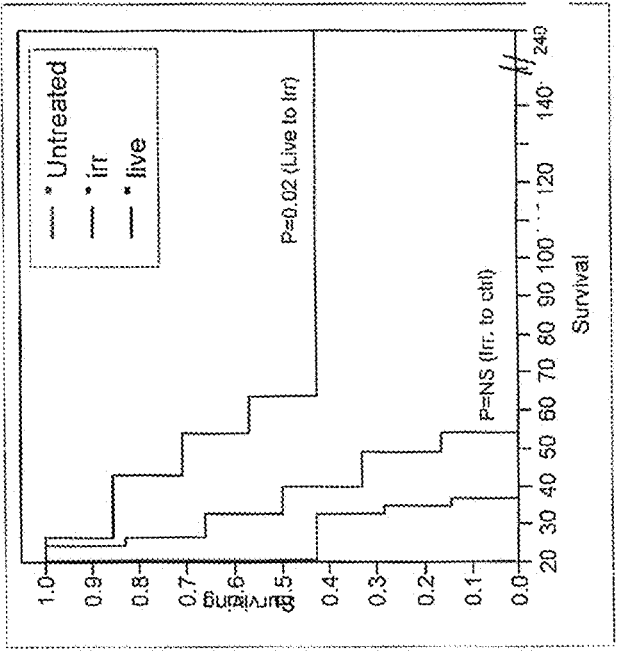
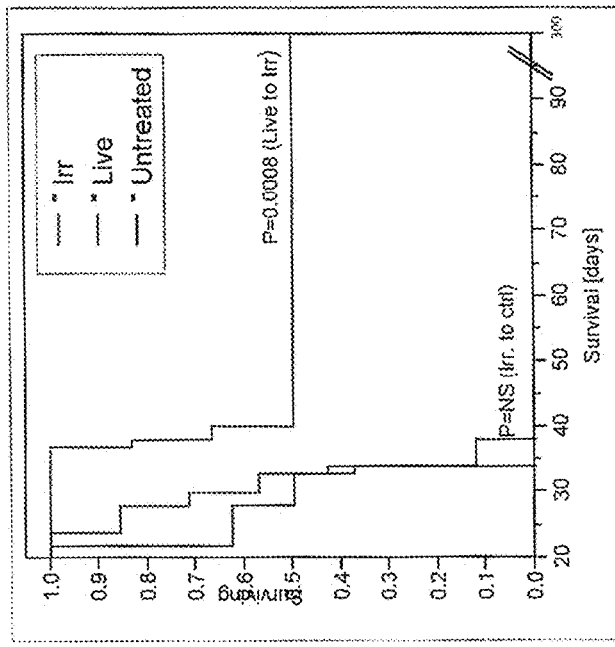

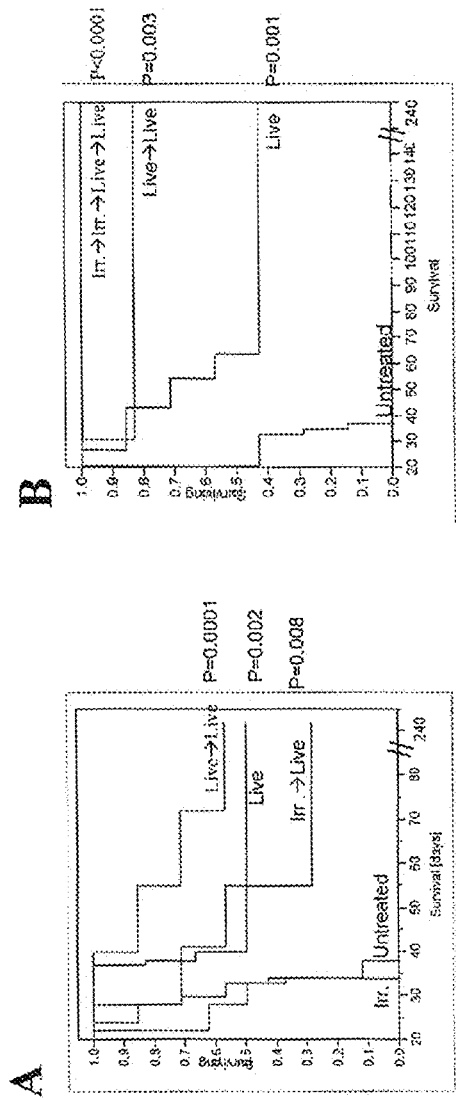
FIGs. 15A-B

METHODS OF TREATING TUMORS IN IMMUNE-PRIVILEGED SITES

RELATED APPLICATIONS

This Application is a National Phase of PCT Patent Application No. PCT/IL2008/001215 having International filing date of Sep. 11, 2008, which claims the benefit of U.S. Provisional Patent Application No. 60/960,041 filed on Sep. 12, 2007. The contents of the above applications are all incorporated herein by reference.

FIELD AND BACKGROUND OF THE INVENTION

The present invention relates to a method of treating tumors in immune-privileged sites.

Cancer is presently the second leading cause of death in developed nations. Despite research that has revealed many of the molecular mechanisms of tumorigenesis, few new treatments have achieved widespread clinical success in treating solid tumors. The mainstay treatments for most malignancies thus remain gross resection, chemotherapy, and radiotherapy. While increasingly successful, each of these treatments still causes numerous undesired side effects. The primary cause of this is that none of these conventional methods specifically targets only diseased cells. For example, surgery, that can remove the primary tumor but not widespread metastasis, results in pain, traumatic injury to healthy tissue, and scarring. Radiotherapy and chemotherapy cause nausea, immune suppression, gastric ulceration and secondary tumorigenesis, and in the case of brain cancers in most cases chemotherapy does not penetrate the blood brain barrier (BBB).

In an effort to develop techniques to more specifically target diseased cells, progress in tumor immunology has led to the discovery of antigens that are preferentially or specifically expressed on cancer cells. These tumor-associated antigens (TAA) or tumor-specific antigens (TSA) have been used as antigenic agents in cancer vaccines designed to stimulate an immune response selectively directed against cancer cells expressing such antigens. See, Tumor Immunology: Immunotherapy and Cancer Vaccines A. G. Dalgleish and M. J. Browning, ods., Cambridge University Press, 1996; Immunotherapy in Cancer, M. Gore and P. Riches, eds., John Wiley & Son Ltd., 1996; Maeurer et al., Melanoma Res., 6:11-24 (1996).

Tumor cells have also been genetically modified to secrete various cytokines, including interleukin 2 (IL-2), IL-8, IL-4, IL-6, gamma-interferon (IFN-γ), and granulocyte-macrophage colony stimulating factor (GMCSF) and have successfully been used in cancer vaccines.

Although tumor vaccines are known to generate potent immune responses against tumors outside the central nervous system (CNS), established tumors within the CNS have failed to respond to such forms of systemic immunotherapy.

The CNS has been shown to accept allografts and xenografts that are otherwise immunologically rejected outside the CNS and thus has been considered an "immunologically privileged" site both historically [Murphy, J. B., and E. Sturm. 1926, Rockefeller Inst. Med. Res 21:183]) and more recently [Tjuvajev, J., et al., (1995) Cancer Res. 55, 1902-1910].

Although being surveyed by most cells in the immune system, the CNS is surveyed less per organ weight. Lymphocytes are found in low numbers in the CNS of healthy humans or animals, and following activation and entry into the brain, T cells encounter a suppressive cytokine environment, or are driven to apoptosis by FAS-FAS-L interactions.

Tumors in the brain are either ignored by the immune system or their growth is insufficiently controlled to prevent intracerebral growth. Immunotherapeutic modalities that were shown effective in treatment of cancers such as melanoma outside the CNS have failed to prevent tumor relapses inside the CNS [Mitchell, M. S. 1989. J Clin Oncol 7:1701]. Some modes of immunotherapy for brain originating tumors in rats even had negative effects on the clinical outcome [Graf, M. R. et al 2003. J Neuroimmunol 140:49].

The various mechanisms limiting immunoreactivity in the brain are incompletely understood, but likely include distinctive anatomic features such as the absence of conventional draining lymphatics, the presence of the blood-brain barrier, limited antigen presentation by microglia and astrocytes and their unique functionality as antigen presenting cells, Fas/Fas-L induced apoptosis of lymphocytes and TGF-β mediated cytokine shift.

Notwithstanding, the immune privileged status of the CNS is not absolute. In experimental allergic encephalomyelitis (EAE) a peripheral immunization with myelin basic protein (MBP) elicits CNS demyelination [Kalman, B., and F. D. Lublin. 1993. Curr Opin Neurol Neurosurg 6:182], suggesting that a systemic effector response can result in a specific immunoreactivity against antigens residing in the CNS. This notion was supported by observations that an effective antitumor response in the CNS can be generated through the use of cytokine-gene modified tumor cell vaccines [Sampson, J. H., et al., 1996. Proc Natl Acad Sci USA 93:10399; Chen, Y., T. et al., 2002, Blood 100:1373] or the transfer of antigen-specific CD8 Cytotoxic T lymphocytes (CTL) [Peng, L., et al 2000. J Immunol 165:5738].

U.S. Pat. No. 6,207,147 teaches an allogenic (histologically incompatible, non-autologous) adoptive transfer of lymphocytes to the patient for the reduction of brain tumors. The lymphocytes are stimulated with tumor cells to provide for their activation. The tumor cells alone are not taught as a method of treating tumors.

The reasons underling rarity of detectable systemic metastases of primary brain tumors is unknown. Approximately 10 cases of spontaneous metastasis of unresected primary GBM were reported in the literature, while the rest of the cases, amounting to less than 0.5% of the patients occurred following the resection of the primary CNS tumor.

As the most malignant primary central nervous systems tumors, high grade anaplastic astrocytoma and glioblastoma multiforme respond poorly to contemporary multimodality treatment programs employing surgical resection, radiation therapy and chemotherapy with a median survival of less than one year after initial diagnosis (Pardos, et al., 1997, Cancer Medicine, 1:1471-1514; Brandes, et al., 1996, Cancer Invest. 14:551-559; Finlay, J. L., 1992, Pediatric Neuro-Oncology, 278-297; Pardos, et al., 1998, Sem. Surgical Oncol., 14:88-95). Consequently, the development of effective new agents and novel treatment modalities against these very poor prognosis brain tumors remains a major focal point in translational oncology research.

SUMMARY OF THE INVENTION

According to one aspect of the present invention there is provided a method of treating cancer in an immune-privileged site of a subject in need thereof, the method comprising systemically administering to an area outside the immune-privileged site of the subject, a therapeutically effective amount of naïve, viable cells of a tumor of the subject, the tumor being in the immune-privileged site so as to generate an immune response in the subject, thereby treating the cancer in the immune-privileged site of the subject.

According to another aspect of the present invention there is provided a pharmaceutical composition comprising as an active ingredient naïve, viable, tumor cells from an immune-privileged site and a pharmaceutically acceptable carrier.

According to yet another aspect of the present invention there is provided a method of treating cancer in an immune-privileged site of a subject in need thereof, the method comprising intravenously administering to an area outside the immune-privileged site of the subject, a therapeutically effective amount of naïve, inactivated cells of a tumor of the subject, the tumor being in the immune-privileged site so as to generate an immune response in the subject, thereby treating the cancer in the immune-privileged site of the subject.

According to further features in preferred embodiments of the invention described below, the immune-privileged site is selected from the group consisting of a brain, testes, and the anterior chamber of the eye.

According to still further features in preferred embodiments of the invention described below, the systemically administering is effected subcutaneously, intradermally or intravenously.

According to still further features in preferred embodiments of the invention described below, the cells of the tumor are autologous cells.

According to still further features in preferred embodiments of the invention described below, the cells of the tumor are non-autologous cells.

According to still further features in preferred embodiments of the invention described below, the method further comprises administering inactivated cells of the tumor prior to administering the viable cells of the tumor.

According to still further features in preferred embodiments of the invention described below, the inactivated cells are administered under a regimen which comprises 2 or more administrations.

According to still further features in preferred embodiments of the invention described below, the naïve viable cells are administered under a regimen which comprises 2 or more administrations.

According to still further features in preferred embodiments of the invention described below, the cells of the tumor are in a single cell suspension.

According to still further features in preferred embodiments of the invention described below, the tumor is a high grade astrocytoma or glioblastoma.

According to still further features in preferred embodiments of the invention described below, the tumor cells are non-cultured.

According to still further features in preferred embodiments of the invention described below, the cancer originates in the immune-privileged area.

According to still further features in preferred embodiments of the invention described below, the tumor cells are purified.

The present invention successfully addresses the shortcomings of the presently known configurations by providing a method of treating tumors in immune-privileged sites.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a line graph illustrating the spontaneous rejection of subcutaneously implanted F98 tumor. Means of tumor diameter are depicted with standard error bars.

Figure 2:
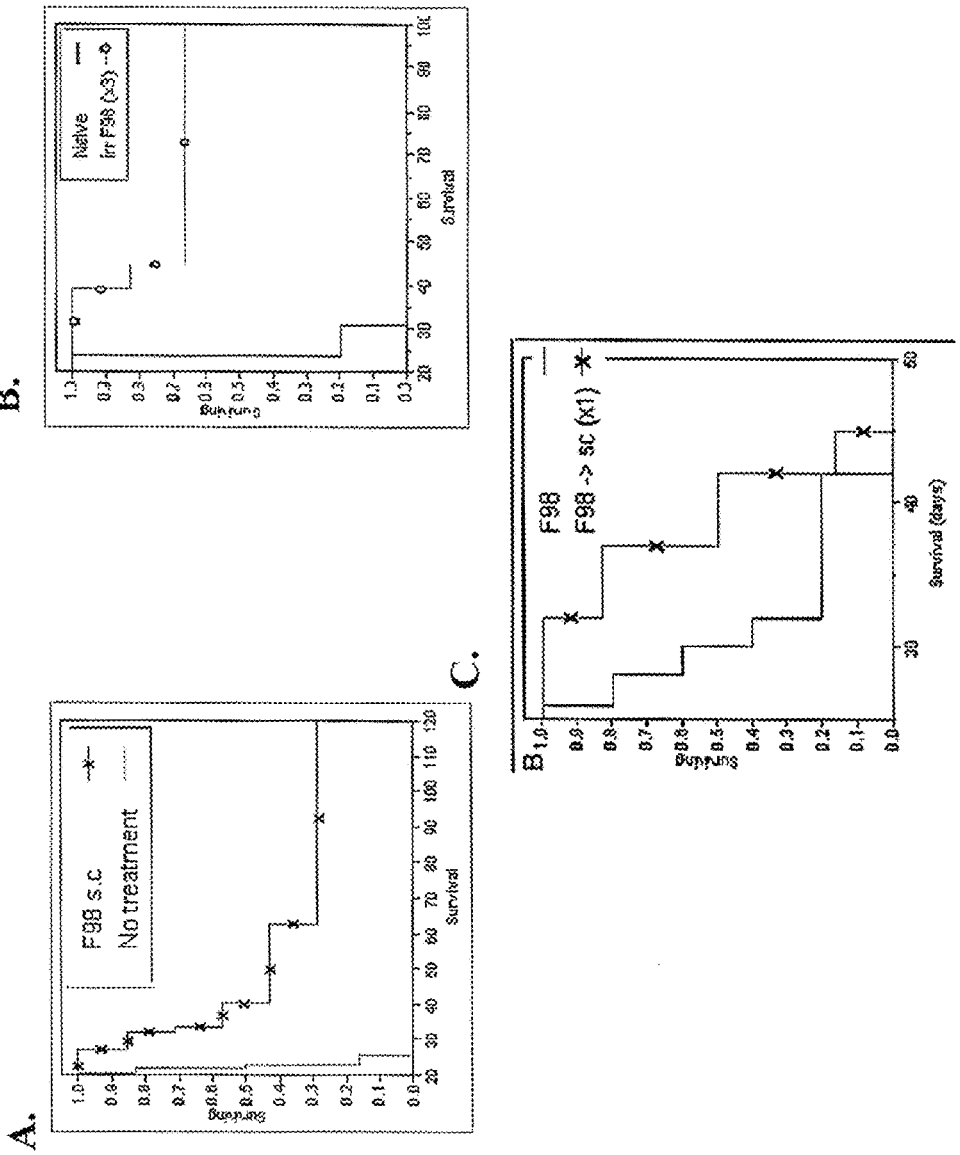

FIGS. 2A-C are Kaplan-Meier survival curves for rats following intracranial administration of F98 cells having received a subcutaneous pre-immunization with live (FIG. 2A) and radiated (FIGS. 2B and 2C) F98 cells. For FIG. 2B rats were immunized with an inoculum of $2 \times 10^6$ irradiated F98 glioma s.c. three times at 14 day intervals. For FIG. 2C, rats were immunized by a single injection of 5000 rad irradiated F98 s.c. ($2 \times 10^6$). The experiment was repeated four times with similar results for live F98 cells and twice for irradiated cells. Survival of treated group was extended in comparison to untreated group (Wilcoxon $P<0.05$).

Figure 3:
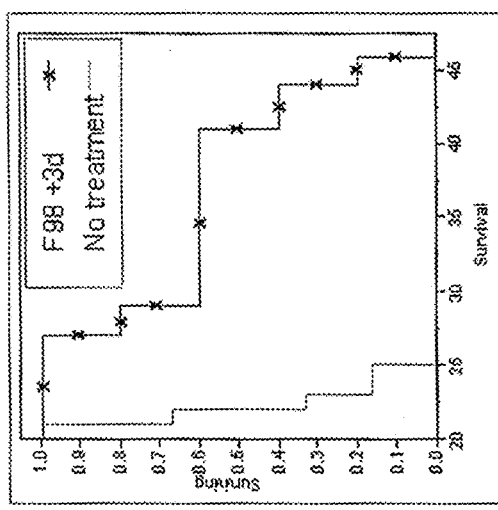

FIG. 3 is a Kaplan-Meier survival curve illustrating an increase in survival for intracerebally, tumor pre-implanted rats following subcutaneous administration of a live F98 tumor. The experiment was repeated twice with similar results.

FIGS. 4A-F are photographs of intestines and lungs of either healthy rats or rats who were injected with $2 \times 10^5$ live F98 tumor either i.p. or i.v. Tumor ridden intestines of two animals dying following an i.p. injection are depicted in FIGS. 4A-B while FIG. 4C depicts normal rat intestines. Tumor ridden lungs of two animals dying following an i.v. injection are depicted in FIGS. 4D-E while FIG. 4F depicts normal rat lungs.

FIGS. 5A-B are Kaplan-Meier survival curves for F98 tumor-bearing rats. A post-mortem was conducted on all animals to determine tumor presence in brains, lung-cavities and in the abdomen cavity. Animals dying with a lung tumor were classified as: 'F98 i.v. (lung tumor)' (lines marked with O—FIG. 5A), animals dying with an intraperitoneal tumor were classified as 'F98 i.p. (tumor i.p)' (lines marked with O—FIG. 5B) otherwise treated animals (injected with live tumors i.v. or i.p. and rejecting these tumors, were termed either 'F98 i.v.' or 'F98 i.p.' (lines marked with X—FIGS. 5A and 5B respectively). Survival of i.v. injected group free of lung tumors (F98 i.v.) was extended as compared to the untreated group (P<0.05 Log-Rank). One animal from the i.v. treated (N=7) survived over 120 days.

FIGS. 6A-B are graphs illustrating the memory and transferability of F98 immunity. FIG. 6A is a point graphs illustrating that rats rejecting an i.c. tumor and surviving ~300d (Rejecting ic) rejected subsequent $5 \times 10^5$ F98 tumor cells s.c. challenge in the flank to a greater extent than the control group. Tumor diameters were measured in individual rats. Mean tumor area is depicted with standard error bars. Statistics: (Rejecting ic) group had smaller tumors (P<0.005 two-tailed student t-test). FIG. 6B is a point graph illustrating the effect of injection of splenocytes either from a naïve rat or splenocytes from a rat rejecting an intracranial challenge into subcutaneously challenged rats. Two groups of four Eight-week old female Fischer rats were inoculated in the flank with $2 \times 10^5$ live F98 Glioma tumor cells. The next day both groups were irradiated 500 rads, and two days after irradiation groups were injected with $10^7$ splenocytes either from a naïve rat or splenocytes from a rat rejecting an intracranial challenge that were co-cultured for four days with irradiated and mitomycin treated F98 tumor cells. Two perpendicular measurements of the tumors were recorded every 2-7 days. An average of these two measurements in individual rats was used to calculate circular tumor area. Means of tumor area are depicted with standard error bars. Significant differences were found in 5/7 time points from day 19 until day 37 (two-tailed student t-test, P<0.05). Three out of four rats in the rejecting-splenocytes treated group and one out of four rats in the naïve-splenocytes treated group were tumor free by day 72.

Figure 7:
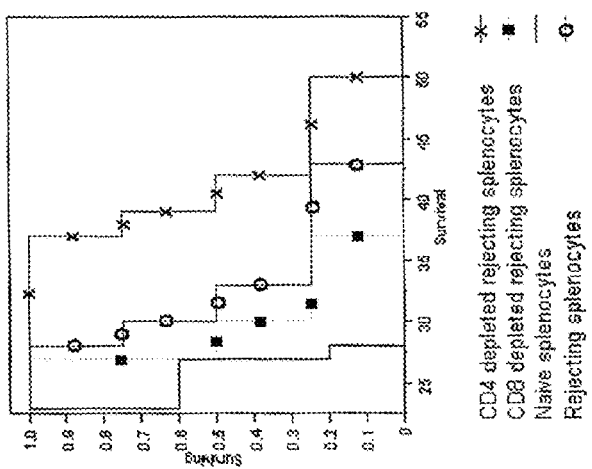

FIG. 7 is a Kaplan-Meier survival curve for F98 tumor-bearing rats. Groups of 4-5, six-week old female Fischer rats were stereotactically injected with $5 \times 10^3$ F98 tumor intracranially. The next day both groups were irradiated 500 rads, and two days after irradiation groups were injected with $10^7$ unsorted splenocytes from a naïve rat (line) or with splenocytes from a rat rejecting an intracranial challenge that were co-cultured for four days with irradiated and mitomycin treated F98 tumor cells (a line marked with O), or with the rejecting rat splenocytes that were MACS depleted either of $CD4^+$ cells (a line marked with X) or MACS depleted of the $CD8^+$ cells (a line marked with colored squares). Survival of rats was followed; Survival of group receiving 'rejecting splenocytes' was higher than that of the control group receiving naïve splenocytes (P<0.02 Log-Rank). Survival of the group receiving $CD4^+$ depleted rejecting splenocytes was higher than of untreated group (P<0.005 Log-Rank). Survival time of the CD8 depleted group was 18% longer than that of control group but marginally insignificant (P<0.09 Log-Rank).

Figure 8:
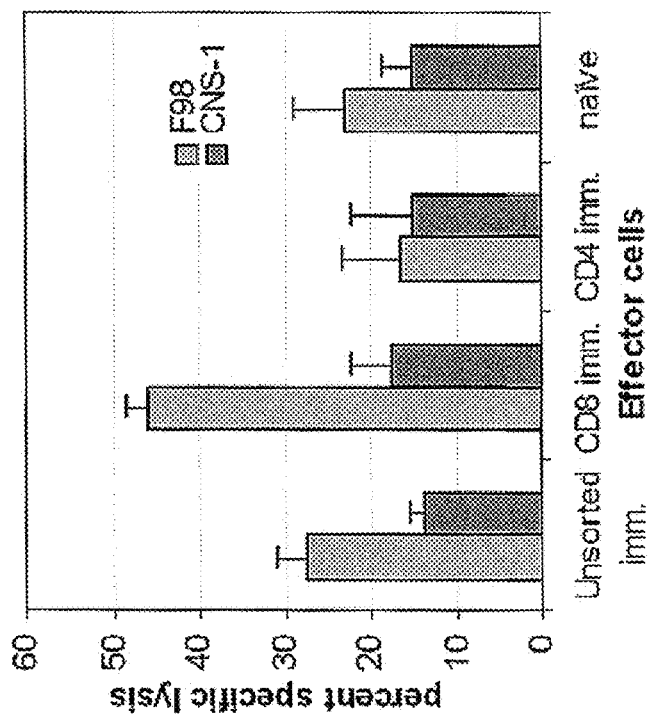

FIG. 8 is a bar graph illustrating the lytic activity of splenocytes from naïve or intracranial tumor-rejecting rats. Splenocytes from a rat rejecting an intracranial challenge were restimulated with irradiated and mitomycin-treated F98 tumor cells. The cells were then purified by MACS sorting for $CD4^+$ (CD4 imm.) or $CD8^+$ cells (CD8 imm.) on MACS separation columns or were left unsorted (Unsorted imm.). These groups and a control naïve splenocyte group (naïve) were assayed in a 16 hr. methionine release cytotoxicity assay. Targets were either the F98 Glioblastoma or the MHC-matched CNS-1 astrocytoma. Results depicted with standard error bar. Statistics: lysis of F98 by unsorted imm. and of F98 by CD8 imm. is stronger than respective lysis of CNS-1 (two-tailed student t-test P<0.05). Lysis of F98 by CD8 imm. is stronger than all other groups apart from F98-unsorted imm. (ANOVA+Tukey Kramer P<0.05).

Figure 9:
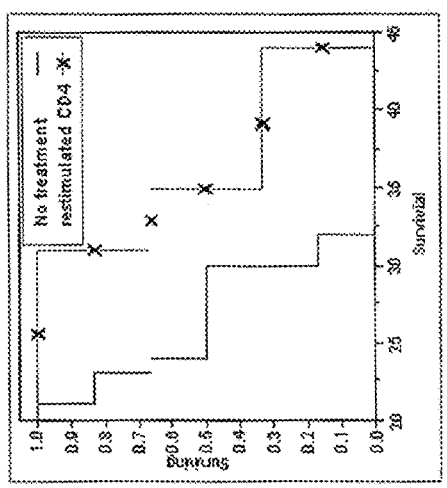

FIG. 9 is a Kaplan-Meier survival curves for F98 tumor-bearing rats: splenocytes obtained from a rat rejecting an intracranial F98 tumor challenge were restimulated with F98 irradiated cells and sorted for $CD4^+$ cells by MACS separation columns. Following a 3-day stimulation, the cells were put in IL-2 containing propagation (rest) medium for four days and were then restimulated with F98 irradiated tumor cells for 3 days and injected ($2 \times 10^6$) i.p. to Fischer six-week old female rats. A few hours later, the treated group and a group of naïve age matched control rats were injected intracranially with $5 \times 10^3$ F98 tumor. Survival of rats was followed; Survival of $CD4^+$ treated group was higher than of untreated group (Log-Rank P<0.05).

Figure 10:
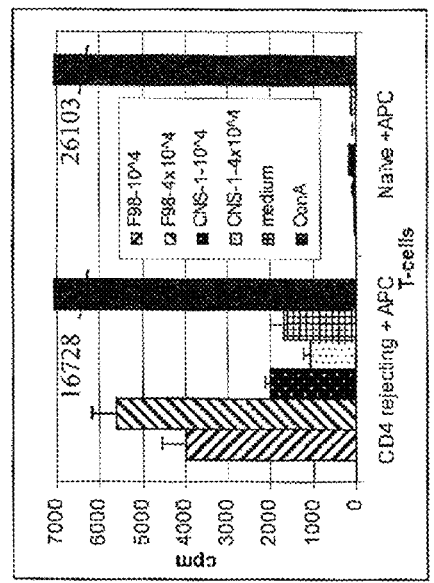

FIG. 10 is a bar graph illustrating the proliferation of $CD4^+$ cells from a rat rejecting intracranial F98 tumor and of naïve splenocytes. CD4+ splenocytes derived by MACS sorting of restimulated splenocytes from a rat rejecting intracranial F98 tumor, or naïve splenocytes were co-cultured with irradiated APC and irradiated F98 tumor for three days. Cells were then washed and transferred to propagation medium for four days and then used in the proliferation assay. Cells were co-cultured either with the irradiated F98 glioma, or the irradiated MHC-matched CNS-1 astrocytoma. After two days wells were pulsed with $H^3$ labeled thymidine. Plates were read on a gas β-counter. Net cpm was derived by subtracting the mean cpm of the irradiated tumor alone from the mean cpm of the corresponding 'tumor+APC+T cells'. Means of net cpm are depicted with standard-error bars. T-cells, either naïve or 'CD4 rejecting' without the addition of irradiated APC had low proliferation rates with cpm readings under 600 for any target (not depicted). The proliferation to different amounts of F98 cells in the 'CD4 rejecting+APC' group was higher than proliferation to medium in that group (ANOVA+Tukey-Kramer P<0.05).

Figure 11:
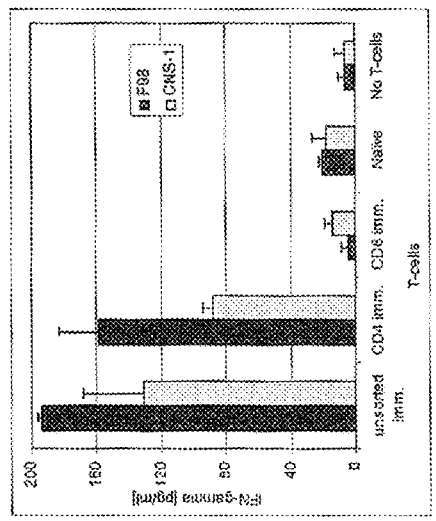

FIG. 11 is a bar graph illustrating the results of an ELISA assay measuring cytokine secretion of splenocytes from naïve or intracranial tumor-rejecting rats: Splenocytes from a rat rejecting an intracranial challenge were re-stimulated for four days on irradiated and mitomycin-treated F98 tumor cells. The cells were then either sorted for $CD4^+$ (CD4 imm.) or for $CD8^+$ cells (CD8 imm.) on MACS separation columns or were left unsorted (Unsorted imm.). The three groups and a control group of naïve splenocytes (naïve) were co-incubated with either an irradiated F98 glioma or with an MHC-matched irradiated astrocytoma (CNS-1). Sixteen hours later supernatants were collected and used in an IFN-γ ELISA assay. Results presented in pg/ml and represent an average of triplicate culture. IFN-γ secretion to F98 in the 'Unsorted imm.' and 'CD4 imm.' Groups was significantly higher than that of naïve (ANOVA and Tukey-Kramer P<0.05). Secretion of 'CD4 imm.' to F98 was higher than to CNS-1 (two-tailed student t-test, P<0.05). Assay was repeated twice with similar results.

FIGS. 12A-I depict immunohistochemical photographs taken from a rat injected with a s.c. and a brain tumor. The figure depicts a s.c. tumor (FIGS. 12A, 12D and 12G), a brain tumor (FIGS. 12B, 12E and 12H) and the contralateral normal brain (FIGS. 12C, 12F and 12I) stained with Hoechst 33342 (blue) staining for cell nucleus, and with antibodies recognizing total T-cells (W3/13)—FIGS. 12A-C, CD8 cells (OX-8)—FIGS. 12D-F and macrophages (ED-1)-detected by the red Cy3-coupled secondary donkey anti mouse antibodies—FIGS. 12G-I.

FIGS. 13A-B are Kaplan-Meier survival curve for Lewis rats. For FIG. 13A Lewis rats were immunized either s.c. three times in the flank at weekly intervals, or twice i.v. in the tail vein at a bi-weekly interval with $2 \times 10^6$ 5000 rad irradiated CNS-1 astrocytoma. Ten days after last immunization rats were injected i.c. with $10^3$ CNS-1 tumor cells. Both the treated groups had extended survival vs. control (Log Rank P<0.005 or less). For FIG. 13B, Lewis rats were inoculated i.c. with CNS-1 astrocytoma. Rats were immunized either once i.v. three days post challenge or twice subcutaneously on day 3 and 8 post challenge with $2 \times 10^6$ 5000 rad irradiated CNS-1 cells. Both treated groups had extended survival vs. control (Log Rank P<0.005 or less).

FIGS. 14A-B are Kaplan-Meier survival curves illustrating the effect of live cell inoculation vs. irradiated cell inoculation on protection against intracranial challenge of tumor cells. FIG. 14A: Rats were injected with $2 \times 10^5$ live or $2 \times 10^5$ irradiated cells subcutaneously 5 weeks prior to an intracranial (i.c.) challenge. FIG. 1B: Irradiated cells ($2 \times 10^6$) were injected subcutaneously (s.c.) two weeks prior to the i.c. challenge while live cells ($2 \times 10^5$) were injected s.c. 11 weeks prior to the i.c. challenge. All rats and control untreated groups were challenged i.c. with ($5 \times 10^3$) F98 cells. Survival of rats is depicted on Kaplan-Meier survival curves. Statistical significance of live cells vs. irradiated cells, or irradiated cells vs. the untreated group is marked on the graph. In both experiments survival of live cell treated group was significantly different to both the untreated group and to the group treated with irradiated cells. In both cases the irradiated cell treated group survival curves was not significantly different to the untreated group.

FIGS. 15A-B are Kaplan-Meier survival curves comparing different clinical protocols for immunization using both irradiated and live cells. Groups of 6-8 rats were injected subcutaneously either with $2 \times 10^5$ irradiated cells (FIG. 15A), or with $2 \times 10^6$ irradiated cells twice followed by live cells twice ($2 \times 10^5$; FIG. 15B) prior to an intracranial challenge with $5 \times 10^3$ F98 cells. Other inoculations were also tested including an inoculation with live cells ($2 \times 10^5$) preceded either by a live cell inoculation ($2 \times 10^5$) or by an irradiated cell inoculation ($2 \times 10^5$—15A, $2 \times 10^6$—15B)—or as a single live-cell treatment (FIGS. 15A-B). Survival of rats is depicted using Kaplan Meir survival curves. Indicated statistical significance was calculated using Log rank test vs. the untreated group. All rats surviving beyond the depicted area in both graphs, survived at least 240 days following intracranial tumor challenge.

Figure 16:
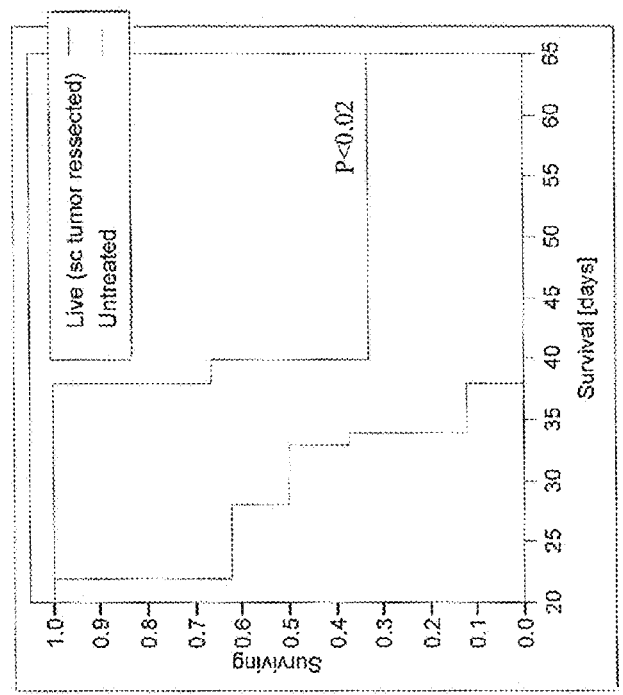

FIG. 16 is a Kaplan-Meier survival curve illustrating that non-rejected F98 tumors removed surgically protect against F98 i.c. tumor challenge. Three rats were injected with $2 \times 10^5$ F98 tumor cells subcutaneously. After 41 days, at which time tumors did not exhibit spontaneous rejection in the rats, the tumors were surgically removed. Fifteen days following tumor removal, the three rats and a control untreated group (N=7) were challenged i.c. with $5 \times 10^3$ F98 cells and followed for survival. Statistical significance is indicated on the Kaplan Mayer survival curve.

Figure 17:
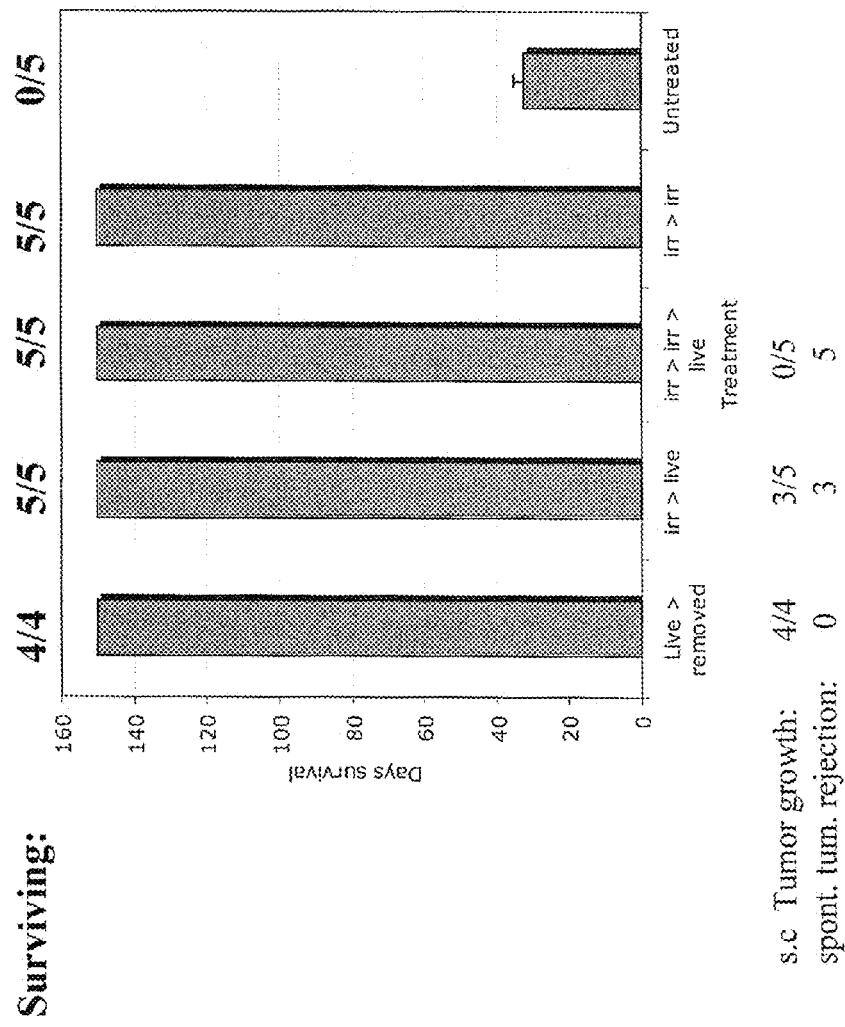

FIG. 17 is a bar graph illustrating that non-spontaneously rejected CNS-1 tumors in Lewis rats removed surgically protect against a CNS-1 i.c. tumor challenge. Groups of 4-5 rats were injected subcutaneously either with irradiated CNS-1 cells ($2 \times 10^6$) or with live cells ($5 \times 10^4$) or with combinations of both irradiated and then live cells, as indicated in the graph. All rats and a control untreated group were challenged with CNS-1 ($10^3$) cells intracranially. Survival of rats is depicted in Bar graph with standard error bars. Statistical significance between all groups and the untreated group is P=0.005 or less (Log Rank). All rats surviving beyond the depicted area in the graph, survived at least 270 days following intracranial tumor challenge.

Figure 18A:
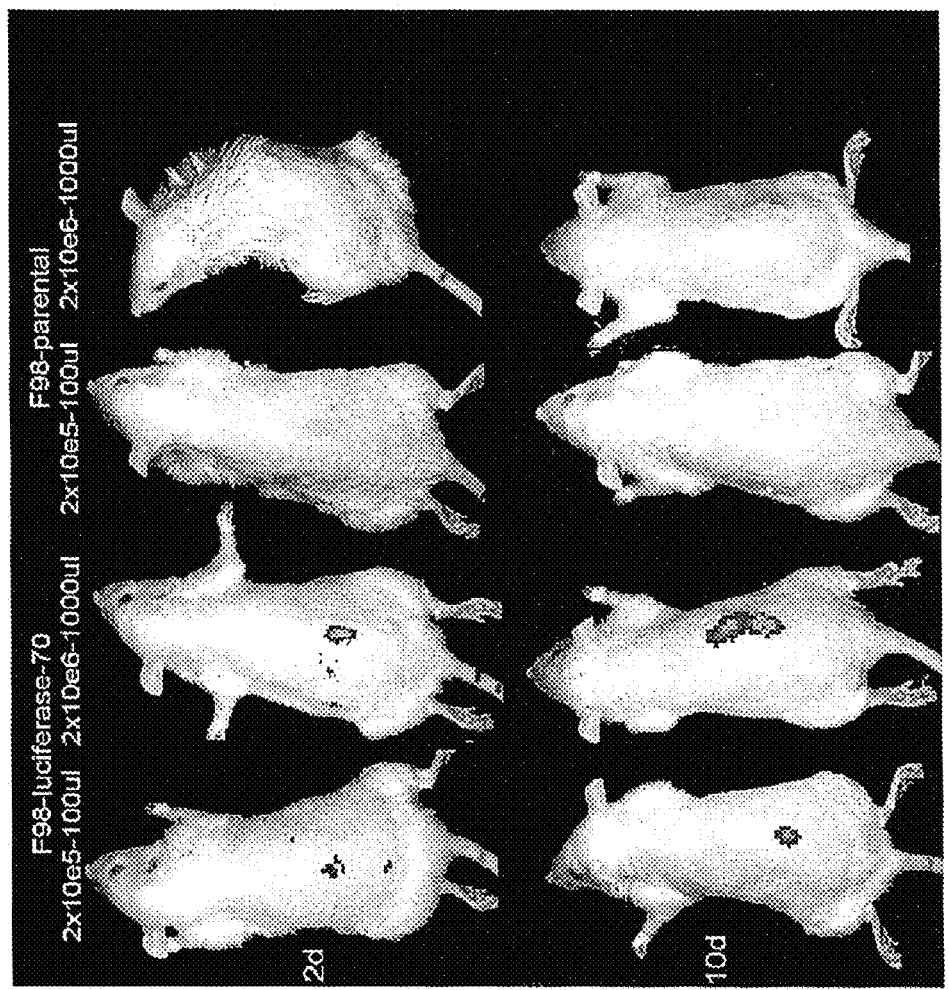
Figure 18B:

FIGS. 18A-B are intra-vital images of rats as analyzed following injection of a an F98 tumor stably transfected with the firefly luciferase gene. The figures comprise black and white image of the rats, overlayed with color enhanced tumor luminescence images. FIG. 18A comprises sequel images of the same representative rats taken after 2 days and 10 days post subcutaneous tumor injection. FIG. 18B comprises images taken after 16 days and 23 days post injection.

Figure 19:
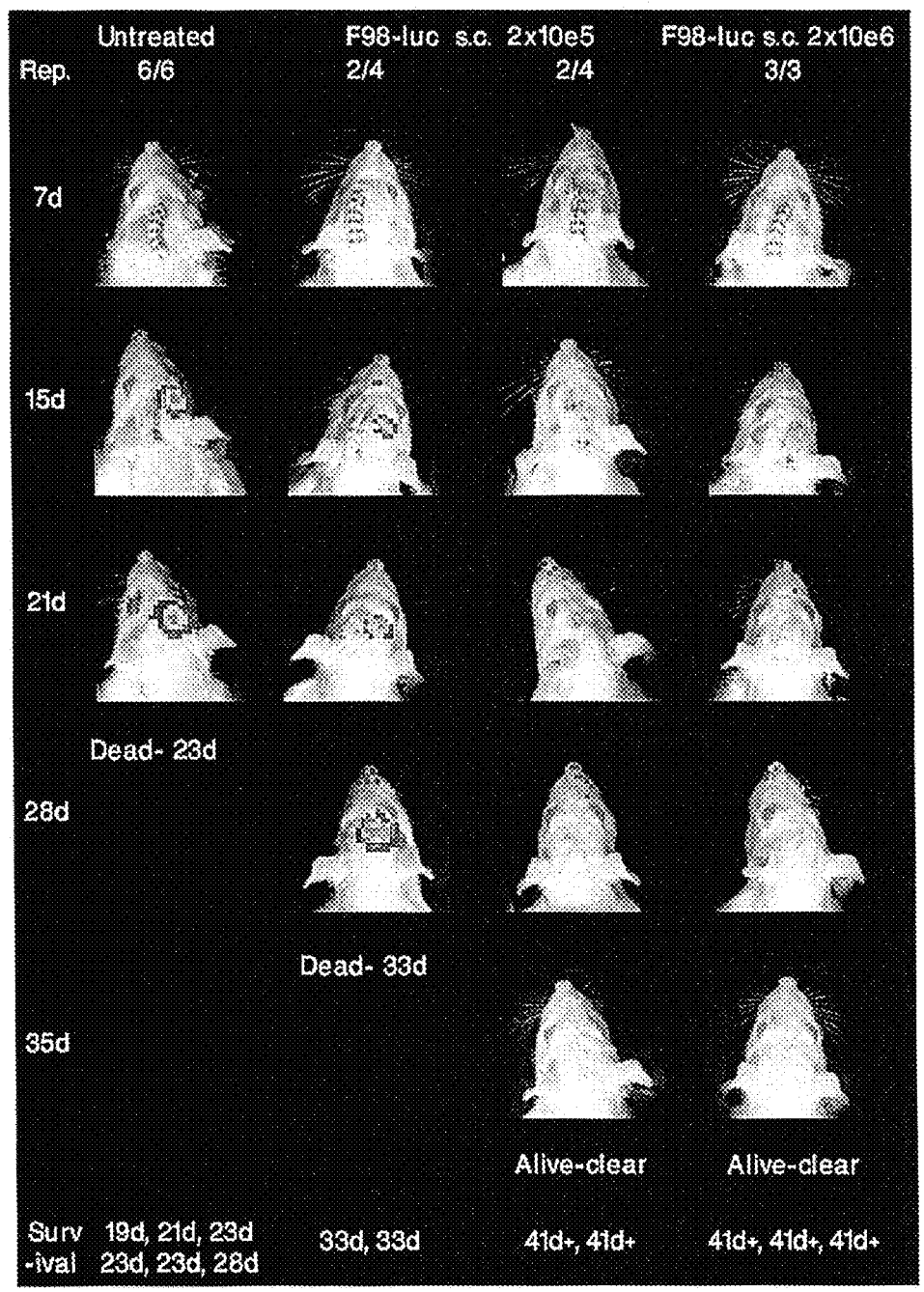

FIG. 19 are intra-vital head images of representative rats, each exhibiting the median survival of their group or its subgroup. Luciferase transfected F98 tumors were traced following intracranial injection: Thirty days following subcutaneous injection and complete rejection of either $2 \times 10^5$ or $2 \times 10^6$ F98-luc cells, the two injected groups and an untreated group of rats were challenged i.c. with $5 \times 10^3$ F98-luc cells. Rats were followed weekly using the IVIS optical system for tumor luminescence. Survival of all the rats in each group, recorded at 41 days, appears below each group or subgroup. The very weak luminescence appearing in some cases in the tips of some animals' noses are unspecific IVIS artifacts, likely due to consumption of plant (chlorophyll) containing food. The assay was repeated twice with similar results.

Figure 20:
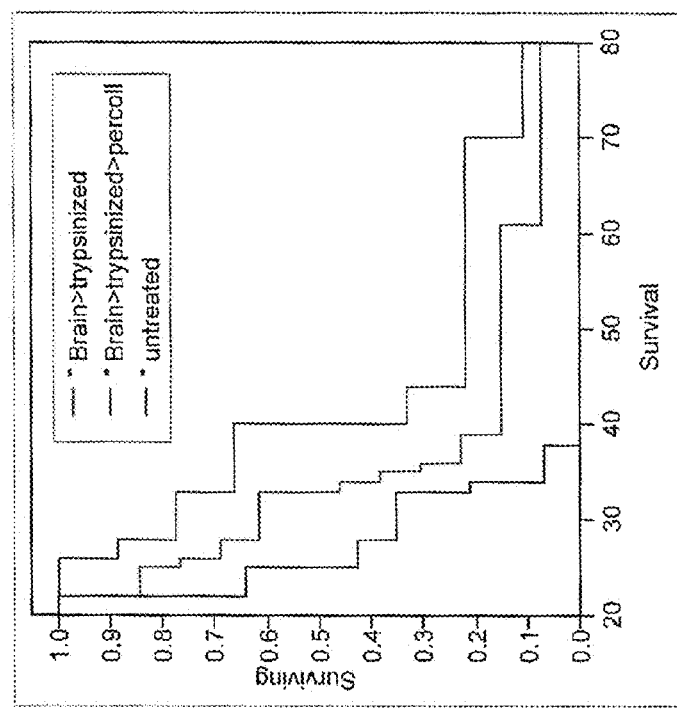

FIG. 20 is a Kaplan-Meier survival curve illustrating use of single cells obtained from brain tumors vs. density gradient separated tumor cells. F98 tumors from brains of rats were harvested and broken down to viable single cells using trypsin. A portion of these cells was run on a three-step percoll gradient. The cells collected on the 1.05 g/ml to 1.08 g/ml interphase, were washed and used as s.c. vaccine. Another group was injected s.c. with the same amount ($10^5$) of viable percoll-unseparated brain-tumor derived cells. Following s.c. tumor acceptance and rejection, all animals and a control untreated group were challenged with F98 tumor cells ($5 \times 10^3$) i.c. Survival data from two experiments are summarized using Kaplan Mayer survival curves.

DESCRIPTION OF THE PREFERRED EMBODIMENTS

The present invention is of methods and pharmaceutical compositions for treating tumors in immune-privileged tissues (e.g. brain tumors).

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Tumor vaccines are known to generate potent immune responses against tumors originating from non-central nervous system (CNS) tumors. However, established tumors originating within the CNS have failed to respond to such forms of systemic immunotherapy.

The various mechanisms limiting immuno-reactivity in the brain are incompletely understood, but likely include distinctive anatomic features such as the absence of conventional draining lymphatics, the presence of the blood-brain barrier, limited antigen presentation by microglia and astrocytes and their unique functionality as antigen presenting cells, Fas/Fas-L induced apoptosis of lymphocytes, TGF-β mediated cytokine shift and immune suppression.

Whilst conceiving the present invention, the present inventors noticed that only 0.5% of patients with CNS tumors have extracranial metastasis, almost all of which are found in immuno-compromised hosts. Incidental data shows that patients having extracranial metastasis (by inadvertent escape of tumor cells following resection) live approximately 60% longer than those not having extracranial metastasis.

These facts led the present inventors to query the immune consequences of placement of live CNS tumor cells outside the CNS. The present inventors unexpectedly and surprisingly found that whereas a live tumor challenge in one site (here an immune privileged site) is lethal, it's placement in another site (i.e., outside of the immuno-privileged site), generates systemic immunity. The present inventors showed that this immunity could spread to the original site in which the tumor is lethal, i.e. the brain, increasing survival of tested animals and in some cases causing complete tumor regression. Presently, common belief holds that inoculation of a live vaccine is too dangerous for clinical applications unless it has been altered in some way so as to enhance its immunogenicity. The present inventors have shown that in the case of tumors originating in immune privileged sites, this is not correct. The strategy described herein, is thus a significant departure from previous approaches to cancer immunotherapy in humans.

Figure 1:
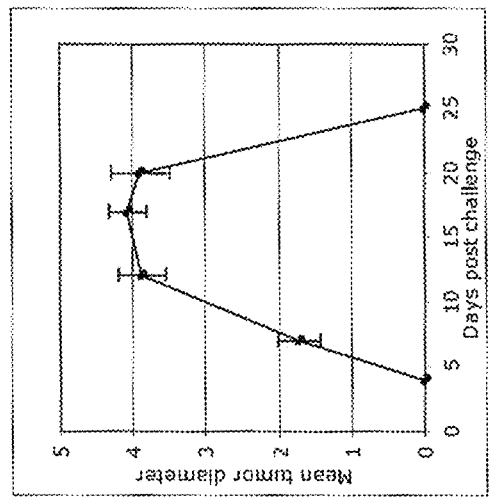

Thus, as is illustrated herein below and in the Examples section which follows, aggressive F98 Fischer rat glioma, placed subcutaneously in rats spontaneously immunologically regresses (FIG. 1). This regression dramatically enhances survival of rats either pre-implanted with tumor intracranially (FIG. 3) or injected with tumor intracranially following a subcutaneous tumor regression (FIGS. 2A-C). The median increase in survival was approximately 80% for both.

Furthermore, the present inventors showed that subcutaneous administration of either live or irradiated tumor cells were effective at inducing an immune response in the brain (FIG. 2B). In addition, the vaccines of the present invention were shown to be effective in reducing brain tumors following intravenous administration to non privileged sites (FIGS. 4A-F).

Anti-CNS tumor immune responses have been generated through the use of cytokine-gene modified tumor cell vaccines [Sampson, J. H., et al., 1996. Proc Natl Acad Sci USA 93:10399; Chen, Y., T. et al., 2002, Blood 100:1373]. Sampson et al use live transfected tumor cells that originate from a non-immune privileged tissue (Melanoma skin cells). The present invention utilizes non-transfected (naïve) tumor cells from immune-privileged tissues.

Chen et al also use live transfected brain tumor cells. Chen et al teach that the systemic administration of non-transfected T9C3 tumor cells results in tumor generation at the site of administration. Thus, Chen et al teach away from the method of the present invention. T9 is a gliosarcoma, which indicates that the tumor is of connective tissue origin [Shibuya N, et al., J Neuropathol Exp Neurol. 1984 July; 43(4):426-38. It is plausible therefore that the tumor used by Chen did not originate from a bona fide immune privileged tissue.

Blumbach (WO 96/05866) teaches vaccines of live tumor cells transduced with: a) a gene coding for an immunostimulatory protein; b) a cytokine; and c) a thymidine kinase gene. The composition is provided as live cells which can grow in vivo and stimulate a response, and then be selectively killed via the thymidine kinase.

In sharp contrast to the present invention, the effectiveness of such vaccines is due to their genetic modification so as to enhance immunogenicity.

The advantage of the present invention over that taught by Sampson et al, Chen et al and Blumbach (WO 96/05866) is that no prior treatment or activation of the tumor cells is required to induce an immune response. Consequently, the tumor cells are not diminished in their therapeutic efficacy (e.g. change in antigenic expression due to even short term culturing of brain tumor cells) as a result of manipulation over time.

U.S. Pat. No. 6,207,147 teaches an allogenic (histologically incompatible, non-autologous) adoptive transfer of lymphocytes to the patient for the reduction of brain tumors. The lymphocytes are stimulated with tumor cells to provide for their activation. The tumor cells alone are not taught as a method of treating tumors.

Thus, according to one aspect of the present invention, there is provided a method of treating cancer in an immune-privileged site of a subject in need thereof, the method comprising systemically administering to an area outside the immune-privileged site of the subject, a therapeutically effective amount of naïve, viable cells of a tumor of the subject, the tumor being in the immune privileged site so as to generate an immune response in the subject, thereby treating the cancer in the immune-privileged site of the subject.

As used herein the term "treating" refers to preventing, alleviating or diminishing a symptom associated with a tumor-bearing disease. Preferably, treating cures, e.g., substantially eliminates the tumor, increases survival time, or at least reduces the tumor size and other symptoms associated with the tumor.

As used herein, the phrase immune-privileged site" refers to a site in the body which is known to accept non-allogeneic (non-histocompatibile) tissue grafts. Such sites include the brain, the anterior chamber of the eye, and the testes Tumors of the present invention preferably express antigens capable of stimulating the peripheral immune system.

Without being bound to theory, it is believed that the lack of tight immune surveillance in an immune-privileged site allows the unimpeded expression of antigens that are suitable targets for immune cells in the periphery. By exposure of the tumor in peripheral tissues where immune surveillance is more intense, the tumor antigens are immunogenically detected. The activated immune response may then spread to the immune privileged site and thus confer immune protection in the tumor's tissue of origin. It is also plausible that some antigens expressed by brain tumors are not under the regulation of immune tolerance mechanisms, limiting immune responses to most self antigens.

Preferably, the cancer originates in the immune privileged site.

Examples of brain tumors which may be treated according to this aspect of the present invention include, but are not limited to glioma and glioblastoma, neuroma and neuroblastoma, gangliomas, medulloblastoma, craniopharyngiomas, pineal region tumors or tumor having mixed components.

Examples of eye tumors which may be treated according to this aspect of the present invention include, but are not limited to retinoblastomas and intraocular melanomas.

Examples of testicular tumors which may be treated according to this aspect of the present invention include, but are not limited to mixed germ cell tumors, hydroceles, seminomas, teratomas and teratocarcinomas.

According to a preferred embodiment of this aspect of the present invention, the tumor is a glioblastoma.

As used herein the term "subject" refers to any (e.g., mammalian) subject, preferably a human subject.

As mentioned hereinabove, the method of the present invention is affected by systemically administering naïve viable tumor cells which are typically situated in an immune-privileged site to an area outside the immune-privileged site.

As used herein, the term "naïve" refers to cells that have not been genetically, physically (e.g. irradiated) or chemically modified. Preferably, the cells are not modified in any other way to bring about a change in their immunogenicity. Thus, for example, the tumor cells of the present invention are not genetically modified to secrete cytokines or chemically activated to increase immunogenicity such as chemical modification with materials such as haptens or dinitrophenyl (DNP).

As used herein, the term "viable" refers to tumor cells that are capable of growth. As illustrated in FIGS. 2A-B, live tumors were more efficacious than irradiated tumors at eliciting an immunogenic response.

Without being bound to theory, it has been postulated that the differences between inoculation with live tumors and immunization with irradiated tumors arise form the difference in the time of exposure of tumor antigens to the immune system, as live tumor cells are present for approximately 3 weeks (as the cells divide from a small tumor which is subsequently rejected completely) while antigen from the irradiated cells might be present for shorter periods of time. The changes might also stem out of the differences in the antigenic profile of the live vs. the irradiated cells, There also might be other qualitative differences between using live and irradiated tumor cells as an immunization protocol.

Tumor cells are generally sampled by a surgical procedure, including but not limited to biopsy, or surgical resection or debulking. Solid tumors can be dissociated into separate cells (i.e. single cell suspension) by physical manipulation optionally combined with enzymatic treatment with such enzymes as Hyaluronidase DNAase, Collagenase, Trypsin, Dispase and Neuraminidase and the like. The cells may then be transferred into fresh physiological or growth medium. Cells may be stored until further use, for example, by freezing in liquid nitrogen.

Preferably, the original tumor cell preparation is performed without cell propagation (i.e. non-cultured), since it is possible that a critical tumor antigen will be lost through the culturing process.

However, the present inventors also envisage expanding the tumor cell population, especially when the original tumor mass is small, to ensure an adequate supply. Cells may be cultured in a growth medium suitable for propagation, optionally supplemented with growth factors. Conditions for reliably establishing short-term cultures and obtaining at least $10^8$ cells from a variety of tumor types is described by Dillman et al. (1993) J. Immunother. 14:65-69. The cell population may also optionally be cloned to obtain a clinical sample of well-defined parameters.

Tumors obtained from patients comprise many different cell types. For example, tumor cells may be surrounded by normal brain cells, by fibroblasts, endothelial cells, macrophages, etc. It may be preferable to purify the tumor cells i.e. enrich for a particular cell type within the tumor cells—e.g. glioma cells. This might serve to enhance the immune response generated by the tumor cells inoculum, and to reduce the possibility of inadvertently causing an autoimmune disease. An exemplary method for enriching is as follows: Initially, tumor cells may be screened to ascertain a set of markers that may discriminate tumor from non-tumor cells. Preferably membranal markers are used on live cells, as staining for intracellular markers would require fixation and permeabilization, processes that kill the cells.

Exemplary antibodies that may be used in such screening techniques (and also purification techniques) include but are not limited to: antibodies to normal oligodendrocytes, astrocytes, and oligo/astrocyte precursor cells [(M)-indicates a membranal antigen] (e.g. Myelin associated glycoprotein-MAG. Proteolipid protein-PLP (M), Sulfatide-O4 (M), O10, Vimentin (M), Neuron specific enolase, Epidermal growth factor receptor-EGFR (M), Platelet-derived growth factor—PDGF, PDGF receptor-PDGFR (M), Neuronal cell adhesion molecule (M)); unique oligodendrocytes markers: (e.g. Myelin Basic Protein—MBP, Galactocerebroside-GalC or O1 (M); Unique astrocytes markers: (e.g. Glial fibrillary acidic protein-GFAP, 5100; Neuronal precursor and progenitor markers: (e.g. Vimentin, Nestin, MAP-2, NFP160 and various neurotransmitter receptors; Microglial markers: (e.g. CD11c (M), CD45 (M), CD68 (M)); Endothelial cell surface markers: CD-31 (M)), Unique Astrocytoma grade II-IV markers: (e.g. Aquaporin1-AQ1 (M), Topoisomerase 2A—TOP2A, Vesicle-associated membrane proteins (VAMP) and VAMB, Caveolin1, Chitinase 3-like 2-CHI3L2 (M) and CHI3L1, Serum amyloid A1—SAA1 (M), NeuromedinB, ATP-binding cassette, subfamily C—ABCC, Secreted modular calcium-binding 1-SMOC-1, SPARC/osteonectin, Matrix Gla protein-MGP (M), Thymidilate synthetase—TYMS, Vascular cell adhesion molecule-1-VCAM1 (M), CD24 (M), Glutathione peroxidase-3-GPX3 (M), Chondroitin sulfate proteoglycan-BCAN (M), Insulin-like growth factor binding protein 7-IGFBP7 (M), Stabilin 1-STAB1 (M), Glycoprotein nmb—GPNMB (M). Expression profiles of stage II-IV astrocytomas are found in Genie website www.cgapdotncidotnihdotgov/SAGE.

Next, a selection step may be performed. This step can be performed using various physical, chemical, and biological methods such as, but not limited to: sorting by FACS, purifying using density gradients and sorting by Magnetic columns (MACS, iMagnet etc.) deletion of irrelevant cells by complement, etc.

Thus, according to another embodiment, the tumor cells are purified prior to administration. As described in Example 14, tumor cells purified using a density percoll gradient, showed an enhanced efficacy compared to tumor cells that were not purified The naïve tumor cells of the present invention are preferably autologous since subject-specific antigens are usually very unique and usually serve as better targets than those shared by other subjects, although non-autologous tumor cells are also contemplated. Preferably, the non-autologous tumor cells comprise the same type of tumor as that being treated. Thus, for example if a patient has a glioblastoma, preferably the non-autologous tumor cells comprise glioma tumor cells. Preferably, the non-autologous tumor cells posses at least one HLA allele compatible with the patient.

According to one embodiment of the present invention, inactivated tumor cells may be administered as well as viable tumor cells. Preferably the inactivated tumor cells are administered prior to administration of the viable tumor cells.

As used herein, the phrase "inactivated tumor cells" refers to naïve tumor cell that have been rendered incapable of no more than three rounds of cell division to form progeny. The cells may nonetheless be capable of response to stimulus, or biosynthesis, antigen presentation, and/or secretion of cell products such as cytokines. Methods of inactivation are known in the art. Preferred methods of inactivation are treatment with toxins such as mitomycin C (preferably at least 10 μg/mL; more preferably at least about 50 μg/mL), or irradiation (preferably with at least about 5,000 cGy, more preferably at least about 10,000 cGy, more preferably at least about 20,000 cGy). Cells that have been fixed or permeabilized and are incapable of division are also examples of inactivated cells.

The naïve tumor cells of the present invention can be administered together with activated lymphocytes (e.g. splenocytes) so as to enhance the immune response thereto. As illustrated in Example 5, immunity against tumors in immune-privileged sites was shown to be transferable by lymphocytes. Preferably, the lymphocytes are autologous. The activated lymphocytes may be administered in combination with the naïve tumor cells of the present invention or at a later or earlier time.

As mentioned hereinabove, the cells of the present invention are administered to an area outside of the immuno-privileged site. Suitable modes and routes of administration are provided hereinbelow.

Various regimens of administration are contemplated by the present invention. For example, an exemplary regimen comprises administering live cells on two separate occasions. The live cell administration may be preempted by at least one administration of irradiated cells. According to one embodiment a period of time of about one week, two weeks, three weeks, four weeks or more is waited between each inoculation. The naïve tumor cells of the present invention can be administered to an organism per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the tumor cells accountable for the biological effect.

Hereinafter, the phrases "physiologically acceptable carrier" and "pharmaceutically acceptable carrier" which may be interchangeably used refer to a carrier or a diluent that does not abrogate the biological activity and properties of the administered compound. The carrier may also include biological or chemical substances that modulate the immune response.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration into the area outside the immuno-priveleged site include systemic delivery, including intramuscular, intradermal, subcutaneous, intravenous and intraperitoneal injections. Preferably, the tumor cells of the present invention are administered subcutaneously or intravenously.

Both the pharmaceutical composition and the mode of delivery should be compatible with maintaining cell viability. Thus, the gauge of the syringe should be selected not to cause shearing and the pharmaceutical composition should not comprise any component toxic to cells etc.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer or inert growth medium.

The pharmaceutical composition described herein may be formulated for parenteral administration, e.g., by bolus injection or continuous infusion.

Pharmaceutical compositions suitable for use in context of the present invention include compositions wherein the active ingredients are contained in an amount effective to achieve the intended purpose. More specifically, a therapeutically effective amount means an amount of active ingredients (tumor cells) effective to prevent, alleviate or ameliorate symptoms of a disorder (e.g., cancer) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from animal studies. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide sufficient immune activation to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks months or years or until cure is effected or diminution of the disease state is achieved.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above. The active ingredient may be prepared in such a way that it may be viably transferred to a distant location.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Spontaneous Regression of Subcutaneously Injected F98

The F98 glioma is an anaplastic glioma of Fischer (F344) rat origin with an aggressive biological behavior similar to that of human glioblastoma multiforme. The tumor is a chemically induced tumor and was shown to be refractory to a variety of therapeutic modalities. Its invasive pattern of growth and uniform lethality following an inoculum of as few as 10 tumor cells make it a particularly attractive model to test new therapeutic modalities.

The following experiment was performed in order to demonstrate the spontaneous rejection of subcutaneously implanted F98 tumor.

Materials and Methods

Animals: Fischer F344 rats were obtained from Harlan Israel. Animals were grown in an SPF environment.

Cells and culture F98 undifferentiated glioma is a chemically induced glioma syngeneic to the Fischer rat. Cells were obtained from the American Type Culture Collection (ATCC) and maintained in DMEM medium supplemented with 4 mM L-glutamine, 1.5 g/L sodium bicarbonate, combined antibiotics, 4.5 g/L glucose and 10% FCS.

Experimental procedure: Twenty-one six-week old female Fischer rats were inoculated in the flank with $2\times10^5$ live F98 glioma tumor cells. Two perpendicular measurements of the tumor were recorded every 2-4 days. An average of these two measurements in individual rats was considered the tumor diameter. The experiment was repeated four times with similar results.

Results

As illustrated in FIG. 1, subcutaneous administration of F98 tumor, results in initial growth of the tumor (0.5-1 cm), followed by shrinkage and spontaneous rejection in all challenged rats. The tumor was well established by two weeks, during which time it was able to draw a substantial amount of blood supply to its parenchyma.

Example 2

Assessing Protection of Subcutaneously Administered F98 Glioma Tumor Cells on Subsequent i.c. Challenge The following experiment was performed to determine whether spontaneous rejection of subcutaneously administered live F98 glioma tumor cells could enhance survival of rats subsequently challenged intracranially with F98 glioma tumor cells.

Materials and Methods

Inoculation/immunization s.c.: Rats (6 weeks and older) were shaved at the flank and injected subcutaneously with 50 µl of live ($2\times10^5$ F98 cells) or $2\times10^6$ irradiated tumor cells (5000 rad). For irradiated tumor cells, rats were vaccinated s.c. three times at 14 day intervals with $2\times10^6$ 5000-rad irradiated F98 cells or were immunized by a single injection of 5000 rad irradiated F98 s.c. ($2\times10^6$). Tumor size in individual rats was followed by measurement of two perpendicular measurements of the tumors. Rats with tumors above 3.5 cm in mean diameter were euthanized.

Inoculation of tumors intracranially: Intracranial administration of live F 98 cells was initiated 7-10 days after the subcutaneously administered tumor cells were rejected, (other experiments showed similar significant results even 40-50 days after subcutaneous tumor rejection). Intracranial administration of irradiated F98 cells was initiated six weeks after the last immunization. Rats were anesthetized with 80-125 μl (depending on strain and age) of 1:2 of Xylazine 2% (Vitamed) and Ketamine 100 mg/ml (Fort Dodge). Anesthetized animal heads were fixed in a stereotactic apparatus, their head fur shaved and skin opened. A hole was drilled with a microdrill at a point 2 mm anterior to the bregma and 4 mm lateral (right) to the midline. $5 \times 10^3$ F98 tumor cells were suspended in 2 μl of PBS and were slowly infused to a point 4 mm deep of the skull with a fine Hamilton syringe. Following the injection, the open skull was cleared with 70% alcohol swab and head-skin was closed with 9 mm Autoclips (Clay Adams) stainless steel wound clips. Procedures were all performed in a sterile environment. Survival of animals was monitored every 1-2 days, moribund animals were euthanized according to regulations.

Results

As illustrated in FIG. 2A, pre-treatment of the rats with live tumor increased median survival from 23 days to 41 days (178%) and the mean calculated by day 120 was approximately 3 times in the treated group than in the control group. Two out of seven rats (29% in this experiment) in the s.c. treated group survived over 5 times the mean of untreated group, and were considered tumor-free. The overall tumor free fraction in all the protection experiments conducted was approximately 25% of rats in treated and none in the control groups.

FIG. 2B illustrates that irradiated tumor cells injected s.c. dramatically extend the survival of rats prophylactically injected with irradiated cells. By day 120 4/6 (67%) treated rats survived tumor free, while the rats in the control group all died during day 24-31.

When immunizing with a single dose of $2 \times 10^6$ irradiated F98 (FIG. 2C) mean survival was significantly increased (124%). In comparison to the results achieved following inoculation with live tumor (167%) inoculation with irradiated tumors in this instance, were less effective. It is plausible that the differences between inoculation with live tumors and immunization with irradiated tumors arise form the difference in the time of exposure of tumor antigens to the immune system, as live tumor cells are present for approximately 3 weeks while antigen from the irradiated cells might be present for shorter periods of time. There also might be a qualitative difference between using live and irradiated tumor cells as an immunization protocol.

In a clinical perspective, the use of irradiated cells allows a safer modality of immunization with an excised brain tumor in humans. Repetitive immunizations as used here might represent an effective method by which to employ these immunizations. It is plausible that the combination of an immunization with irradiated tumor followed by the inoculation with live tumor might provide an efficient way to combine the safety and initial-immunity achieved by irradiated tumors and the effectiveness of treating with live tumors.

Example 3

Assessing Immunotherapy of Established F98 i.c. by Live F98 Injection s.c.

The following experiment was performed to assess whether subcutaneous injection of F98 could improve survival of rats with established F98 brain tumors.

Materials and Methods

Six-week old female Fischer rats were stereotactically injected with $5 \times 10^3$ F98 tumor intracranially as described hereinabove. Three days following injection rats either received an inoculum of $2 \times 10^5$ F98 glioma s.c. in the flank (cross) or were left untreated (line).

Results

As illustrated in FIG. 3, injection of a live F98 tumor s.c. increased survival of rats pre-implanted with the tumor intracerebrally. Survival increased by 167%, although complete loss of tumor was more infrequent in the immunotherapy models than in the protection models.

Example 4

Challenging with F98 in Locations Other than s.c

The following experiment was performed in order to ascertain whether immunity to tumors originating from an immune privileged site can be achieved by translocation of these live tumors to a non privileged site other than the subcutaneous area.

Materials and Methods

Animals were injected either s.c., i.v. or i.p. with $2 \times 10^5$ live F98 tumor, and 45 days following primary injection, all surviving rats were rechallenged with F98 intracranially (apart from one rat out of six in the i.p. injected group which died before challenge). A post-mortem was conducted on all animals to determine tumor presence in brains, lung-cavities and in the abdomen cavity.

Results

Both i.v. and i.p. immunizations with live F98 proved more hazardous than s.c., as roughly half of the animals in both groups died from either an abdominal tumor following an i.p. injection (FIGS. 4A and 4B) or with lung tumors following an i.v. injection (FIG. 4D). FIGS. 4C and 4F depict, respectively, normal abdomens and lungs.

The two modes of immunization had two different outcomes for the surviving portions of rats following the rechallenge with intracranial F98. Four out of seven rats injected i.v. that had no lung metastasis, had a significant prolonged survival compared to the naïve injected group. The i.v. injected group tripled its mean survival in comparison to that of the naïve injected group, with 1/4 rats surviving over 120 days (FIG. 5A). In contrast, the i.p. immunization had no significant effect on animal survival (FIG. 5B), with one animal dying before the F98 rechallenge.

Example 5

Transferability of F98 Immunity by Immunized Rat Splenocytes

Since there was an extended time period between initial subcutaneous injections to secondary intracranial challenge, it is plausible to assume that this immune response is a memory-type response, and thus could be attributed to the adaptive immune arm. Accordingly, the following experiments were performed to ascertain whether the immunity may be transferable by splenocytes to naïve rats. Moreover the mechanisms by which different immune cell subsets operate to eradicate tumors was assayed.

Materials and Methods

Cells and cell culture: F98 cells were cultured as described above. The CNS-1 astrocytoma is a chemically induced glioma syngeneic to the Lewis rat. The CNS-1 line was provided by William F. Hickey, Dartmouth Medical Center, Lebanon, New Hampshire, USA. The line was grown in RPMI medium supplemented with 4 mM L-glutamine, combined antibiotics, and 10% FCS.

Separation of lymphocytes on MACS magnetic beads: MACS technique (Miltenyi Biotec GmbH-Bergish Gladbach, Germany), was used to separate CD4+ or CD8+ cell populations for various assays. The effluent of the CD4 or CD8 columns, depleted of either CD4+ or CD8+ cells respectively, and also the CD4+ or CD8+ positive populations removed from the magnetic columns were checked by flow cytometry for purity. Purity of separations from unwarranted cells (i.e. CD4+ cells in the CD8+ preparation) was typically above 99%. The procedure was performed according to manufacturer's instructions.

In vitro cytotoxicity assays: Spleens of rats were removed and teased to a single cell suspension. Red blood cells (RBC) were removed by RBC removal buffer (Sigma) according to manufacturer's protocol. Splenocytes were restimulated in lymphocyte medium (RPMI, 10% Fetal calf serum (FCS), 2 mM glutamine, combined antibiotics, 1 mM sodium pyruvate, $5 \times 10^{-5}$M β-mercapto ethanol, 1% nonessential amino acids) with tumor cells that had been irradiated (5000 rad) and Mitomycin-C (80 µg/ml/$10^7$ cells) treated.

Following three days of incubation in flasks at 37° C., splenocytes were washed and mixed with $^{35}$S-methionine (10 µCi) labeled target cells. CTL assays were performed in 96 u shaped microtiter wells, at 37° C., 5% $CO_2$ for 5 and 16 hr. Cultures were terminated by centrifugation at 1200 rpm for 8' at 4° C. and 50 µl of the supernatants were transferred to TopSeal™-A, 96 well microplate (Packard), added with Microscint™ 40 (Packard) scintillation fluid and counted in a TopCount microplate scintillation & luminescence counter β-counter.

Percentage of specific cell lysis was calculated as follows: [(cpm of specific wells)−(spontaneous cpm of same target)]/ [(cpm maximal release of target)−(spontaneous cpm of same target)]×100. Spontaneous release was determined by incubation of labeled target cells in lymphocyte medium. Maximal/total release was determined by incubation of target cells in 0.1M NaOH at the last 20' of the assay.

Proliferation assays: Various antigens or irradiated tumor cells (5000 rad) treated with mitomycin (80 µg/ml/$10^7$ cells) were dispensed in stimulation medium (DMEM, 1% normal rat serum (NRS), 2 mM glutamine, combined antibiotics, 1 mM sodium pyruvate, $5 \times 10^5$ M β-mercaptoethanol, 1% nonessential amino acids) in quadruplicates to 96 well plates. T-cells were added ($2.5 \times 10^4$), either with or without 5000 rad irradiated thymocytes ($2.5 \times 10^5$), serving as APC. After two days cells were pulsed ON with 25 µl of pulsing medium containing PBS and methyl $^3$H thymidine (5 Ci/mmol-Amersham) at the ratio of 25:1 respectively. Cultures were transferred to 96 well glass-filter (Packard), added with Microscint™ 20 (Packard) scintillation fluid and counted in a TopCount microplate scintillation & luminescence counter β-counter. Results are expressed as mean counts per minute (cpm)

Proliferation assays were also conducted on MACS positively selected, pure (>99%) populations of CD4 or CD8 cells as effectors.

ELISA assays with irradiated tumors: Following a similar procedure to the proliferation assay, two days following co-culture with irradiated tumors or with antigen, 80 µl of assay supernatant from triplicate or quadruplicate cultures was obtained for an ELISA assay. IFNγ, secretion was determined using standard manufacturer protocols (BD-OptEIA).

Adoptive transfer of immunocytes: Spleens were harvested from animals rejecting an intracranial tumor challenge. Red blood cells were lysed and splenocytes were re-stimulated with irradiated, mitomycin C-treated tumor cells at 1:50 tumor:splenocyte ratio for three days in lymphocyte medium.

Naïve rats were challenged either subcutaneously or intracranially with F98 tumors at indicated doses, the next day rats were irradiated 500 rads total body irradiation (TBI) for non-lethal lymphoablation, and two days following irradiation, groups were injected i.v. with $10^7$ of the above-mentioned splenocytes either unsorted, or depleted of either CD4 or CD8 cells, or injected with unsorted naïve rat splenocytes.

In the CD4 adoptive transfer experiment, CD4 cells were re-stimulated twice with irradiated and mitomycin treated tumor and subsequently injected without the use of irradiation on the same day of intracranial tumor inoculation.

Results

Adoptive transfer of immunocytes: To check for maintenance of an immune memory, rats that had survived an i.c. challenge (~300 d) with F98 were subcutaneously rechallenged. These rats were protected from the F98 following its inoculation s.c. FIG. 6A shows that the rats of the control group had all accepted the tumors and spontaneously rejected them as observed in FIG. 1. In contrast the pretreated rats rejected the tumors much faster and half of the rats had no tumor take.

To determine whether immunity to tumors is transferable by cells, rats were subcutaneously injected with F98 tumor, the following day all rats were irradiated 500 rads Total Body Irradiation (TBI) for non-lethal lymphoablation, after two days groups were replenished either with naïve splenocytes or with splenocytes from a rat rejecting an intracranial tumor that were restimulated for four days with irradiated and mitomycin treated F98 tumor.

As seen in FIG. 6B, the group receiving the rejecting splenocytes had a significantly smaller mean tumor area as compared to the group replenished with naïve splenocytes. The rejecting splenocytes restored the ability to reject a subcutaneous tumor in three out of four rats. In the naïve replenished group only one out of four rats rejected his subcutaneous tumor, while the other animals were culled as the tumor reached an average diameter of 35 mm. The significant difference between the groups was observed only after day-19.

Total body irradiation, used in the transfer experiment, caused animals to lose their natural ability to spontaneously reject the tumor. Even the replenishment of the irradiated hosts with $10^7$ splenocytes did not restore their ability to reject the subcutaneous tumor.

In this and other experiments it was noted that manipulation of the immune system of the rats, even an injection of a T-cell line that does not recognize a tumor antigen, frequently compromised the animals ability to spontaneously reject the tumor s.c. (data not shown). These results are compatible with the results of Graf et al who showed that several immune manipulations of the 9 L gliosarcoma result in increased tumor volumes, and decreased survival of rats [Graf et al, 2003, J Neuroimmunol 140:49].

IL-2 was not used in the in vivo experiment in this or in any other transfer experiments suggesting that the injected effector cells are not dependent on exogenous IL-2 for their function.

Transferability of immunity by T-cell sub-populations: All rats were injected intracranially with live F98 cells, a day later rats were irradiated TBI 500 rads, and after two days were replenished either with $10^7$ naïve splenocytes, with unsorted rejecting cells (splenocytes taken from a rat rejecting an intracranial tumor and restimulated with irradiated mitomycin treated F98), with CD8 depleted rejecting cells (enriched for CD4 cells), or with CD4 depleted rejecting cells (enriched for CD8 cells). As illustrated in FIG. 7, immunity was transferable either by the unsorted rejecting splenocytes or by the CD4 depleted group, containing an enriched population of CD8+ cells, both these groups had significantly extended survival in comparison to naïve-replenished group (131% and 164% survival vs. control respectively). These results suggest that in this case CD8+ cells are pivotal to tumor immunity.

The CD4+ population (CD8 depleted) consistently only showed a mild effect on the survival of rats (Log-rank P<0.09, 118% survival vs. control).

Taken together the results suggest that a passive transfer of immune restimulated cells or the CD8 containing fraction of these cells significantly delays animal death in the i.c. model.

Cytotoxicity of T-cell sub-populations: In order to determine direct killing ability, the different fractions of the rejecting cells were assayed for cytotoxicity in a 4-hour Cytotoxicity assay. FIG. 8 shows that both the unsorted rejecting fraction and the MACS positively sorted CD8 fraction (90% pure CD8 cells devoid of CD4 cells) had a strong differential killing as seen by their lytic profile. The killing of F98 was roughly 2-2.5 times higher towards F98 than to the MHC-matched CNS-1 astrocytoma. Both the naïve and the CD4+ positively sorted fraction had the same killing to F98 than to CNS-1 and a lower cytotoxicity to F98 than found in the two CD8+ containing groups. These results suggest that the CD8+ fraction of the cellular arm is capable of generating a cytotoxic response towards the F98 tumor.

Survival following transfer of CD4 cells from F98 rejecting-rat: The CD4+ sorted fraction of F98-restimulated rejecting rat splenocytes were re-stimulated with irradiated and mitomycin treated F98 tumor and injected ($2 \times 10^6$) into rats at the same day of F98 i.c. challenge. As illustrated in FIG. 9, the restimulated CD4+ cells prolonged rat survival significantly (137% survival for CD4+ treated vs. control).

These results suggest that under some conditions also the CD4+ cell fraction has an effect on the survival following an F98 i.c. challenge, albeit, this effect is less dramatic than the effect of the CD8+ CD4− fraction seen in FIG. 7.

Proliferation of CD4 cells obtained from F98 rejecting-rat The CD4 cells used in FIG. 7 were used in a proliferation assay checking their proliferation towards irradiated F98 or CNS-1 cells. FIG. 10 shows a significant dose-dependent response of the CD4+ rejecting cells but not of the naïve cells to F98 but not to CNS-1. No response was recorded in either group when irradiated thymocytes (APC) were not added to the wells. These results suggest that CD4+ cells can recognize tumor antigens but need indirect presentation for this recognition.

IFN-γ secretion to F98 of T-cell sub-populations: As IFN-γ was shown to have a pivotal role in tumor rejection [Qin, Z., and T. Blankenstein. 2000. Immunity 12:677; Qin, Z., et al, 2003. Cancer Res 63:4095], IFN-γ secretion was measured in response to the tumor by ELISA of co-culture supernatants. Unsorted, four-day F98-restimulated splenocytes from a rejecting rat, and their CD4+ or CD8+ sorted fraction were incubated for 16 hours with the F98 glioma or the CNS-1 astrocytoma in the presence of irradiated APC, naïve splenocytes were used as control. FIG. 11 shows that only the unsorted-rejecting and the CD4+ rejecting fractions, but not the CD8+ rejecting fraction had significant IFN-γ secretion to F98 when compared to the naïve splenocyte response. The CD4+ cell fraction had a significantly stronger response to F98 than to CNS-1. The same pattern of results was observed in an intracellular IFN-γ secretion assay. (data not shown).

Interestingly in both unsorted-rejecting, and CD4+ rejecting groups, the IFN-γ secretion to the MHC matched CNS-1 astrocytoma was significantly higher than in the naïve. This might suggest that the F98 undifferentiated glioma shares expressed antigen/s with the CNS-1 astrocytoma.

Example 6

Immune Cells Penetrate s.c. Tumor and Brain Tumor but not Surrounding Tissue

To check for presence of immune cells in the tumor parenchyma, rats were injected either with a s.c. tumor or with a s.c. tumor and an i.c. tumor or with an i.c. tumor only. One week following tumor/s injection, rats were perfused and brains and s.c. tumors were excised.

Materials and Methods

Immunohistochemistry was conducted on animals perfused with freshly prepared paraformaldehyde (PFA) 4%. Perfused animal tissues (brains and s.c. tumors) were post-fixed with 4% PFA for at least 24 hours. Then 30% sucrose was added 1:1 V:V for cryoprotection. The organs were frozen and cut into 14 μm sections in a floating section microtome, slices were kept in PBS-0.1% Azid. For antigen staining, sections were blocked ON with 20% normal donkey serum and 1% normal rat serum. Section were then washed and stained with different mouse monoclonal antibodies overnight at 4° C. The antibodies were diluted in PBS containing 0.5% bovine serum albumin (BSA). Antibodies used were: ED-1 (CD68-Serotec) (1:500) for rat macrophages, W3/13 (1:500) for total rat T cells, OX-8 (1:250) for rat CD8 cells. The sections were washed twice for 10 min with PBS$^{-/-}$ and incubated with CY3-labeled donkey anti-mouse antiserum (1:5000) (Jackson Immuno-research) ON. Counterstaining of cell nuclei was done with Hoechst 33342. Stained slices were transferred to Superfrost-Plus slides (Menzel Glaser, Germany) and mounted with AquaPolyMount (polysciences, USA).

Results

Injection of a tumor s.c. with or without i.c injection was followed by massive infiltration of T-cells, CD8 T-cells, and macrophages reaching all parts of tumor parenchyma.

Injection of brain tumor was followed by infiltration of T-cells and CD8 cells, and a small number of macrophages. The infiltration was exclusive to the densely nucleated tumor mass and to the close vicinity of the tumor, but not to other parts of the same hemisphere (not shown) or in the same position in the contralateral hemisphere. The penetration of T-cells and CD8 cells into the brain tumor was more pronounced in the s.c. treated rat than in the rat injected only with brain tumor (not shown).

FIGS. 12A-I show that an injection of live tumor s.c. does not cause a widespread inflammation in the brain. T-cells in the brain were not observed when there was no tumor residing in the brain. Whenever tumor was injected i.c. the immune reaction was limited to the tumor and to its closest vicinity.

Example 7

Corroboration of Results in Lewis Rat

To check the assumptions that peripheral immunization with tumors either via the i.v. or the s.c. modes could protect from an i.c. tumor challenge another tumor model was used, the Lewis-rat CNS-1 astrocytoma. As with the F98, also this tumor is syngeneic in (or autologous to) the Lewis host, it is chemically induced and does not carry any known foreign or viral antigens. The biological characteristics of this tumor resemble those of human astrocytomas displaying a single cell infiltration of parenchyma and the ability to spread into leptomeningeal, perivascular and periventricular areas. The tumor is considered an applicable and useful model in neuro-oncology (Barth, R. F. 1998. J Neurooncol 36:91).

Following an extensive unrelated study with the CNS-1 it was noticed that low but constant percentages (5-15%) of rats injected with CNS-1 spontaneously reject the tumors s.c. Moreover injection of a low dose of the live tumor s.c. in the limb was not accepted by the rats and a consequent injection of live CNS-1 s.c. in the flank was accepted and then rejected. These preliminary results suggested that also the CNS-1 tumor might exhibit the phenomenon of split immunity under certain conditions.

Materials and Methods

Animals: Lewis rats were obtained from Harlan Israel. Animals were grown in an SPF environment.

Cell culture: CNS-1 cells were cultured as described above.

Results

Lewis rats were injected with irradiated cells either s.c. or i.v. Results of either the protection experiments or the immunotherapy experiments were similar with very strong protection achieved in both modes of immunization. While i.v. injection of irradiated CNS-1 three days following tumor inoculation increased mean survival by +86% (a single i.v. injection)—FIG. 13A, a prophylactic vaccination increased survival to over twice mean survival time with 43% of the animals surviving over 100 days (FIG. 13B).

Multiple vaccinations s.c. with irradiated CNS-1 tumors protected 80-100% rats from tumor challenge i.c. (rats survived over 150 days) both in the protection (FIG. 13A) and in the immunotherapy assays (FIG. 13B) with all rats surviving over 100 days.

Example 8

Effectiveness of Live Cell vs Irradiated Cell

The following experiment was performed to test the effectiveness of live cell vs irradiated cell vaccine.

Materials and Methods

The experiment was performed essentially as described for Example 2. In the first experiment, Fischer F344 rats were immunized with either $2\times10^5$ live cells, $2\times10^5$ irradiated cells, or were left untreated. In the second experiment, the amount of irradiated cells used was 10 times that of the live cells, i.e.—$2\times10^6$ cells irradiated cells vs $2\times10^5$ live cells.

Results

FIG. 14A demonstrates that while live cells significantly enhanced the survival of the rats, or even cured some of their brain tumors, irradiated cells did not change the survival of the rats vs. the control untreated group. Even when the amount of irradiated cells was increased to ten times the amount of live cells, a significant difference between live and irradiated cells could be observed (FIG. 14B). Live cells significantly enhanced the survival of the rats, or even cured some rats of their brain tumors, while the irradiated cells did not significantly change the survival of the rats vs. the control untreated group. In both assays the survival of the live-cell treated rats was enhanced as compared to the irradiated-cell treated rats.

In conclusion, in both assays the live cell treatment was significantly better than the irradiated cell treatment, both when equal doses of cells were used, and when doses of irradiated cells were 10 times higher than the dose of live cells used for immunization.

Example 9

Immunization Protocol

The following experiment was performed so as to obtain an optimal immunization protocol, both in terms of effectiveness and safety.

Materials and Methods

Groups of 7-8 Fischer F344 rats were immunized with combinations of $2\times10^5$ live cells and $2\times10^6$ irradiated cells. When two or more immunizations of live cells took place, the second injection of live cells was carried out after all tumors from the first injection were spontaneously rejected. For example, in this experiment, the intervals between the injections in the Irr→Irr→Live→Live protocol were 3, 2 and 7.5 weeks respectively.

Results

FIGS. 15A-B show in two separate experiments that groups of rats that were inoculated twice with live cells exhibited enhanced survival and higher percentages of long term surviving/cured rats in comparison to the groups inoculated once with live cells.

To enhance the safety of the immunizations, rats were injected s.c. with irradiated cells either once (FIG. 15A) or twice (FIG. 15B) prior to the injection s.c. with live cells.

When rats were injected s.c. with irradiated cells once and then with live cells s.c. (FIG. 15A), the injected live cells grew in all animals, albeit, tumor diameters were smaller in average when compared at maximal tumor size (P<0.03, t-test—not shown). Complete tumor rejection in irradiated-cell treated rats occurred earlier than when injected into naïve rats (not shown).

In two experiments rats were injected twice with irradiated cells before a live F98 s.c. challenge. In one of the experiments none of the rats (0/8) developed tumors s.c. vs. 13/14 rats that developed s.c. tumors in the naïve injected groups (P<0.00005, Fisher exact—not shown). In another experiment, five of six rats that were immunized twice with irradiated cells developed very small (2.5-3.5 mm) tumors for a period of 1-3 days, as compared to approximately 2-3 weeks of tumor growth until rejection in most naïve injected animals These results indicate that one, but more effectively, two injections of irradiated cells prior to the injection of live cells s.c. either protects the rats completely from the s.c. growth of live tumors, or generates a very quick rejection of these tumors once they appear.

The above results suggest that repeated live inoculations leads to enhanced efficacy, while the repeated immunizations with irradiated cells before the live tumor inoculation leads in most cases to the abrogation of live tumor growth s.c. The results also suggest that a highly protective vaccine could combine the safety of use of irradiated cells, and the efficacy of live cell inoculation.

Example 10

Clinical Responses to an Intracranial. Challenge in Animals that have not Spontaneously Rejected their s.c. Tumors One of the theoretical basis on which the invention stands upon is that in most cases live tumor cells that originate from brain tissue are spontaneously rejected in the periphery. In the F98 tumor model, approximately 97% of the rats (N>200) that received a live tumor challenge s.c. rejected their tumor spontaneously. In one experiment, due to unknown reasons three rats in one group did not reject their s.c. tumors.

A different tumor model—the CNS-1 astrocytoma (glioma) syngeneic to the Lewis rat, is accepted subcutaneously without rejection in approximately 90-95% of cases. In 5-10% of cases, the tumors are accepted s.c. and then spontaneously rejected.

The following experiments were performed in order to ascertain whether the removal of growing s.c. F98 tumors or CNS-1 tumors protects rats from a subsequent challenge with intracranial administration of the identical tumor.

Materials and Methods

F98 tumors: Tumors of three Fischer F344 rats were surgically removed 41 days following inoculation. No residual metastasis was observed in any of the rats following s.c tumor removal. Fifteen days after the s.c. tumor removal, the rats together with a control untreated group, were challenged i.c. and followed for survival.

CNS-1 tumors: Lewis rats were injected with live CNS-1 cells ($5 \times 10^4$ cells). Tumors grew in all rats and were removed 36 days following injection (mean tumor diameter at removal: 13.5±1.5 mm). No residual metastasis was found subcutaneously in any of the rats following tumor removal. Two other groups were injected s.c. either with 70 Gy irradiated CNS-1 cells ($2 \times 10^6$) once or injected with irradiated cells twice before the injection of live cells s.c. Another group was immunized twice with irradiated cells only. All rats and a control untreated group were challenged with $10^3$ CNS-1 cells intracranially and followed for survival.

Results

F98 tumors: The results are depicted in FIG. 16. These results suggest that even in rats that had their tumors removed following uncontrolled s.c. growth (a rare event in this model), the rats survived longer than untreated rats, with 1/3 rats cured of its brain tumor (survival over 330 d).

CNS-1 tumors: FIG. 17 shows mean rat survival with standard error bars. As can be seen, the injection of live CNS-1 tumor cells to rats and the tumor's subsequent removal completely protects the rats from an i.c. challenge with the tumor. Similarly all the other treated groups, either immunized with irradiated cells or with a combination of irradiated cells and live cells were completely protected from a subsequent intracranial CNS-1 tumor challenge.

All the rats injected with live cells had growing tumors that were not spontaneously rejected. The group that was immunized with irradiated cells once followed by a live tumor cell injection s.c. supported tumor growth in 3/5 animals. The small tumors were visible only 1-3 days and were then spontaneously rejected. The group that was immunized twice with irradiated cells and then injected with live cells s.c did not support any s.c. tumor growth. These results corroborate those observed in the F98 model suggesting that the addition of irradiated cells prior to the live cell injection s.c. might abrogate in most cases the growth of the live tumor cells injected subcutaneously. The use of irradiated cells did not compromise the efficacy achieved by the subsequent use of live cells, but rather protected the rats from a s.c. live tumor growth.

Taken together the results suggest that even in the worst case scenario in which live brain tumor cells are injected in an extracranial site and are not spontaneously rejected, following the tumors surgical removal, immunity to an intracranial tumor challenge can still be achieved. The removal of the s.c. tumor generates sufficient immunity that even if some residual tumor cells remained s.c. they will probably also be rejected. The results also indicate that the combination of irradiated and live tumor cell vaccine may provide both the safety provided by the irradiated cells (lack of tumor growth s.c.), and the efficacy conferred by live cells.

Example 11

Follow-up on the Complete Elimination of the Live Tumor Cells Injected s.c

The following experiment was performed to ascertain whether all tumor cells injected s.c. do not metastasize to distant organs and are fully rejected s.c. following their observed visual disappearance.

Materials and Methods

A concern that might be raised using live tumor cells as an immunizing agent is that some cells might remain s.c. even following complete rejection as observed by the eye. To answer this question, the firefly luciferase gene was stably transfected into the F98 tumor. A clone of the F98-luciferase tumor was then followed intra-vitally inside the rat by the tumor's luminescence. Rats were injected with 250 µl of Luciferin, the substrate that is oxidized by the Luciferase expressed by the tumors. This reaction produces visible light. Using this method, even a small number of tumor cells that cannot be felt by fingers or measured visually by clippers can be detected inside the rat, even beyond bone material (such as skull). Intra-vital imaging was performed once a week using the IVIS optical imaging system (see: wwwdotcaliperlsdotcom/products/optical-imaging/).

To follow s.c. and distant organ metastasis following tumor challenge rats were injected either $2 \times 10^5$ live cells in 100 µl volume s.c. (the usual volume and cell quantity used) or injected with $2 \times 10^6$ live cells in 1000 µl volume. The injection of $2 \times 10^6$ live cells in a large volume represents an extreme case scenario in which large amount of live cells are injected s.c. and spread over a large area. As a control, $2 \times 10^5$ non-transfected (parental) live F98 cells (100 µl) and $2 \times 10^6$ (1000 µl) live F98 cells were injected to rat littermates.

Results

FIGS. 18A-B shows that the F98-luciferase injected in both quantities and volumes show some initial spread in the s.c. area 2 days following injection. The tumors grew in only one location, reaching their maximal size by 10 days, and were all completely rejected by 23 days. The growth and the complete spontaneous rejection of the two doses—$2 \times 10^5$ and the $2 \times 10^6$ F98-luciferase inoculates had similar tumor growth and rejection dynamics.

The injected parental F98 tumor—both $2 \times 10^5$ (1000) and $2 \times 10^6$ (10000) inoculate, showed similar growth and rejection dynamics to the F98-Luciferase transfected cells. The complete rejection, in similar growth dynamics to the F98-luciferase, of both doses of the parental F98 corroborates the F98-luciferase tumor model as a relevant model to follow tumor growth dynamics.

The IVIS system is more sensitive than eyes/hands as small residual tumors could be observed, on occasion, even 7-10 days after the tumors could not be observed visually or felt manually.

No distant organ metastases were observed in the immunocompetent rats in the two similar experiments conducted. Similarly, no s.c. tumor metastasis were found in any rats following the tumor's complete visually observed rejection (N=11 rats) or 7-10 d thereafter.

Example 12

Follow-up of Intracranial Tumor Growth and its Elimination by Large Proportion of the Rats Injected with Live Tumor Cells s.c.

The following experiment was performed to follow dynamics of tumor cell growth and rejection following intracranial inoculation with F98-luciferase (luc) cells.

Materials and Methods

To follow the dynamics of tumor growth following intracranial challenge, groups of rats were inoculated subcutaneously either with $2\times10^5$ live F98-luc cells, or with $2\times10^6$ live F98-luc cells. After one month, all s.c. tumor inoculated rats lost their s.c. tumors, both visually, as measured by clippers, and as observed using the IVIS system. One month following s.c. inoculation, all rats and a control untreated group were challenged i.c. with $5\times10^3$ live F98-luc cells. Rats were followed using luciferase luminescence in the IVIS system each week.

Results

FIG. 19 shows sequel head pictures of rats that had the median survival of their group or their subgroup. As can be observed, all the untreated animals (6/6) quickly succumbed to the i.c. tumor (mean±STD 22.8 d±3 d) with large tumors developing with very similar dynamics in all rats. From the animals that were injected subcutaneously with $2\times10^5$ live cells, one half (2/4) developed intracranial tumors. The tumors that developed in these animals grew at slower rate compared to those of the untreated group, as per observed tumor luminescence. Intracranial tumor size and luminescence in the F98-luc model highly correlates [Bryant, M J. 2008. J Clin Neurosci 15:545-551]. The other half (2/4) of the $2\times10^5$ F98-luc treated animals subgroup did not to develop any i.c. tumor by 41 days. None of the animals (3/3) that were injected s.c. with higher amount of live cells ($2\times10^6$ cells) developed intracranial tumors.

These results suggest that live cell immunization either slows or abrogates completely intracranial tumor growth.

This experiment further shows that a dose-response effect to the live cells—the animals responded better to a s.c. inoculate of $2\times10^6$ live cells than they did to a s.c. inoculate of $2\times10^5$ live cells.

Statistical significance calculated for both the $2\times10^5$ s.c. F98-luc. treated group, and the $2\times10^6$ F98-luc treated group showed significant enhancement of survival as compared to the untreated group, with P values of 0.004 and 0.01 (Log-rank) respectively.

Example 13

Tumor Breakdown to Single Cells

The following experiment was performed to find a reagent or a combination of reagents that would allow for glioma breakdown into a viable, high-quality preparation of single cell suspension.

Materials and Methods

Five materials were assayed; DNase, Collagenase, Hyaluronidase, Papain and Dispase II. Tumor breakdown experiments were performed in the following way: Human glioma tumors were weighed, cut into small pieces using scissors and diluted in HBSS (+Ca +Mg) to 100 mg tumor pieces/ml. Enzymes were added to the tumors according to the concentrations set forth in Table 1, herein below. Dispase II and Papain were added as single reagents, while DNase and Collagenase were added in different concentrations, with or without Hyaluronidase. All cell preparations were gently triturated after 30 min, 60 min, and 2 hours using a Pasteur pipette.

Results

Several experiments on human gliomas showed that the use of Dispase II as a single reagent produces high quality cell preparations with very high percentage of surviving cells (around 100%). This was apparent when tumor pieces were incubated for 30 minutes or even up to 20 hours with dispase II. All combinations of DNase and Collagenase with or without Hyaluronidase produced good results but these were systematically inferior in comparison to the tumor breakdown results obtained with dispase II.

All three concentrations of Dispase II used produced similar good breakdown results, although a 30-60 minutes incubation with low to medium concentrations of Dispase II produced the optimal tumor breakdown results.

The results are set forth in Table 1, herein below.

TABLE 1

| Conc. Used | Low (L) | Med (M) | High (H) | Results |
|---|---|---|---|---|
| DNase I | 5 u/ml | 13 u/ml | 20 u/ml | Combination of the three |
| Collagenase D | 0.035% | 0.05% | 0.12% | enzymes in various |
| Hyalonidase | 600 u/ml | 1000 u/ml | 2500 u/ml | concentration 30' to 20 hour breakdown gave variable results ranging from good breakdown to acceptable breakdown. |
| Dispase II | 0.6 u/ml | 1.5 u/ml | 2.4 u/ml | Excellent breakdown with ~100% cell survival during 30' to 20 hour breakdown |
| Papain | 2 u/ml | 5 u/ml | 20 u/ml | Bad breakdown with very low cell survival |

Example 14

Tumor Purification

The following experiment was performed to check the efficacy of using single cells obtained from brain tumors as a cell source of a vaccine as compared to using density gradient-separated cells obtained from the same tumor cell preparation.

Materials and Methods

F98 tumor cells from tissue culture were run on a percoll gradient to determine their specific density. It was found to be between 1.05-1.06 g/ml. Next, rat brain tumors were collected, broken down using trypsin and ran on a discontinuous 3-step gradient. (1.08, 1.05, 1.00). Tumor cells were collected from between the 1.05 and 1.08 g/ml interphases. The cells were washed in PBS and injected ($10^5$) into a group of rats. Another group of rats was injected with a similar number of live single cells from the tumor without separation on a percoll gradient.

Results

FIG. 20 represents a summary of two similar experiments. The figure shows that using nonpurified tumor cells as vaccine enhances median survival of rats to controls by 32% (P=0.047 to control), while using percoll gradient separated cells as a vaccine inoculate enhances survival by almost twice that amount (60%) with a more highly significant P value (P=0.0009). FACS analysis of cells following the percoll purification step (not shown) showed that the purification was only partial, Notwithstanding, the separation stage still enhanced the vaccine efficiency.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of treating a brain tumor of a subject in need thereof, the method comprising systemically administering to an area outside the brain of the subject, a therapeutically effective amount of naïve, viable cells of a tumor obtained from the brain of the subject, so as to generate an immune response in the subject, wherein said naïve, viable cells of said tumor of the subject are administered without non-autologous cells, thereby treating the brain tumor of the subject.

2. The method of claim 1, wherein said systemically administering is effected subcutaneously, intradermally or intravenously.

3. The method of claim 1, further comprising administering inactivated cells of said tumor prior to administering said viable cells of said tumor.

4. The method of claim 3, wherein said inactivated cells are administered under a regimen which comprises 2 or more administrations.

5. The method of claim 3, wherein said naïve viable cells are administered under a regimen which comprises 2 or more administrations.

6. The method of claim 1, wherein said cells of said tumor are in a single cell suspension.

7. The method of claim wherein said tumor is a glioma, astrocytoma or glioblastoma.

8. The method of claim 1, wherein said tumor cells are non-cultured.

9. The method of claim 1, wherein said naïve, viable cells of said tumor are purified.

10. The method of claim 9, wherein said naïve, viable cells of said tumor are density gradient purified.

11. A method of treating a brain tumor of a subject in need thereof, the method comprising systemically administering to an area outside the brain of the subject, a therapeutically effective amount of naïve, viable cells of a tumor obtained from the brain of the subject, so as to generate an immune response in the subject, thereby treating the brain tumor of the subject, wherein said administering is effected following the provision of inactivated cells of said tumor to the subject.

12. The method of claim 11, wherein said inactivated cells are administered under a regimen which comprises 2 or more administrations.

13. The method of claim 11, wherein said naïve viable cells are administered under a regimen which comprises 2 or more administrations.

14. A method of treating a brain tumor of a subject in need thereof, the method comprising systemically administering to an area outside the brain of the subject, a therapeutically effective amount of purified, naïve, viable cells of a tumor obtained from the brain of the subject, so as to generate an immune response in the subject, thereby treating the brain tumor of the subject.

15. The method of claim 14, wherein said naïve, viable cells of said tumor are density gradient purified.

* * * * *